United States Patent
Crum et al.

(10) Patent No.: US 10,983,034 B2
(45) Date of Patent: Apr. 20, 2021

(54) ASSEMBLY FOR STORING AND TRANSPORTING TISSUE SAMPLES IMMERSED IN A FLUID

(71) Applicant: Ventana Medical Systems, Inc., Tucson, AZ (US)

(72) Inventors: Nathan Crum, Marana, AZ (US); Michael Otter, Tucson, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 764 days.

(21) Appl. No.: 15/681,235

(22) Filed: Aug. 18, 2017

(65) Prior Publication Data

US 2018/0128718 A1 May 10, 2018

Related U.S. Application Data

(63) Continuation of application No. PCT/EP2016/053341, filed on Feb. 17, 2016.
(Continued)

(51) Int. Cl.
*G01N 1/00* (2006.01)
*G01N 1/30* (2006.01)
(Continued)

(52) U.S. Cl.
CPC .......... *G01N 1/30* (2013.01); *A61B 10/0096* (2013.01); *B01L 3/502* (2013.01); *B01L 3/545* (2013.01); *G01N 1/31* (2013.01); *B01L 3/50825* (2013.01); *B01L 2200/0689* (2013.01); *B01L 2300/021* (2013.01); *B01L 2300/047* (2013.01); *B01L 2300/049* (2013.01); *B01L 2300/0848* (2013.01); *B01L 2400/0478* (2013.01); *B01L 2400/0605* (2013.01); *B01L 2400/0611* (2013.01); *B01L 2400/0616* (2013.01);
(Continued)

(58) Field of Classification Search
None
See application file for complete search history.

(56) References Cited

U.S. PATENT DOCUMENTS

| 5,490,971 A | 2/1996 | Gifford et al. |
| 8,829,473 B1 | 9/2014 | Griswold et al. |

(Continued)

FOREIGN PATENT DOCUMENTS

| CN | 1160829 A | 10/1997 |
| CN | 1360668 A | 7/2002 |

(Continued)

OTHER PUBLICATIONS

International Search Report and Written Opinion dated Jul. 11, 2016 for corresponding PCT/EP2016/053341 filed Feb. 17, 2016, 18 pages.

*Primary Examiner* — Jyoti Nagpaul
(74) *Attorney, Agent, or Firm* — Charney IP Law LLC; Thomas M. Finetti

(57) ABSTRACT

A method and system for processing a sample in a fluid is provided. An assembly comprising a cap prefilled with a fixative solution, a valve, and a container for storing a tissue sample are provided. The valve is adapted to be situated between the cap and the container such that fluid can flow from the cap into the container when the assembly is upright, but the fluid cannot backflow from the container to the cap when the assembly is horizontal or inverted.

19 Claims, 30 Drawing Sheets

Related U.S. Application Data

(60) Provisional application No. 62/165,616, filed on May 22, 2015, provisional application No. 62/118,878, filed on Feb. 20, 2015.

(51) Int. Cl.
*B01L 3/00* (2006.01)
*G01N 1/31* (2006.01)
*A61B 10/00* (2006.01)

(52) U.S. Cl.
CPC ............ *B01L 2400/0622* (2013.01); *B01L 2400/0633* (2013.01); *B01L 2400/0644* (2013.01); *B01L 2400/0683* (2013.01)

(56) References Cited

U.S. PATENT DOCUMENTS

| | | |
|---|---|---|
| 2004/0038269 A1 | 2/2004 | Birnboim |
| 2004/0234423 A1 | 11/2004 | Dehmer |
| 2005/0047963 A1 | 3/2005 | Safar et al. |
| 2007/0140915 A1 | 6/2007 | Sakai et al. |
| 2008/0210689 A1 | 9/2008 | Rodewald |
| 2009/0155923 A1 | 6/2009 | Bonecker |
| 2010/0311165 A1 | 12/2010 | Ram et al. |
| 2012/0137586 A1 | 6/2012 | Timmons |
| 2013/0178804 A1* | 7/2013 | Tennican ............ A61M 39/18 604/218 |
| 2014/0120531 A1 | 5/2014 | Biadillah et al. |
| 2014/0213934 A1 | 7/2014 | Ellis |

FOREIGN PATENT DOCUMENTS

| | | |
|---|---|---|
| CN | 101356008 | 1/2009 |
| CN | 203757090 U | 8/2014 |
| JP | 2007225399 | 9/2007 |
| JP | 2009519439 A | 5/2009 |
| JP | 2011221030 A | 11/2011 |
| JP | 2014522489 A | 9/2014 |
| JP | 2016520817 A | 7/2016 |
| WO | 00/77429 A1 | 12/2000 |
| WO | 2007/053870 A2 | 5/2007 |
| WO | 2012163992 A1 | 12/2012 |
| WO | 2012171529 A1 | 12/2012 |
| WO | 2014081877 A1 | 5/2014 |
| WO | 2014172241 A1 | 10/2014 |

\* cited by examiner

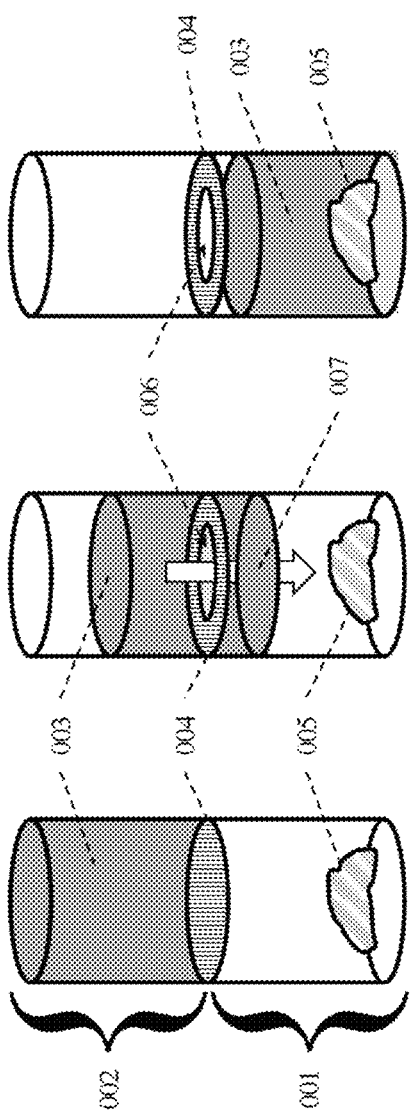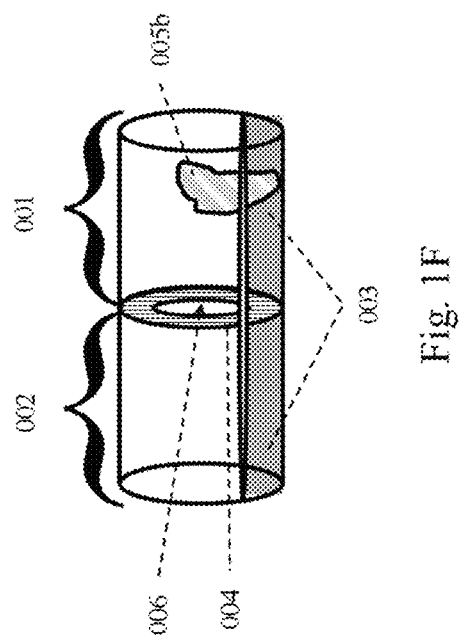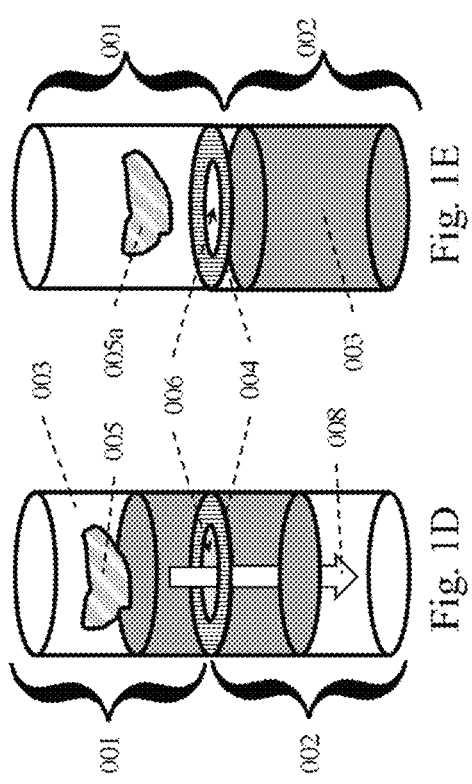

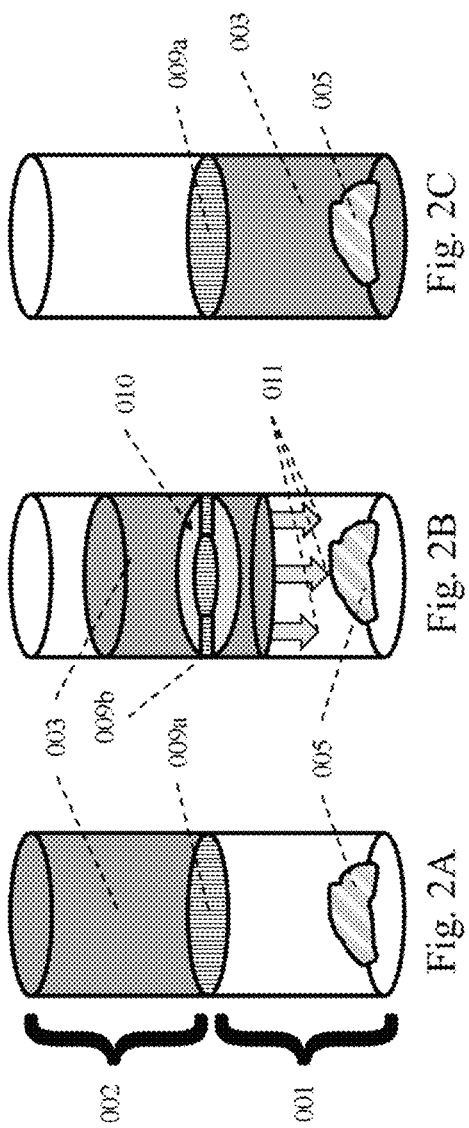
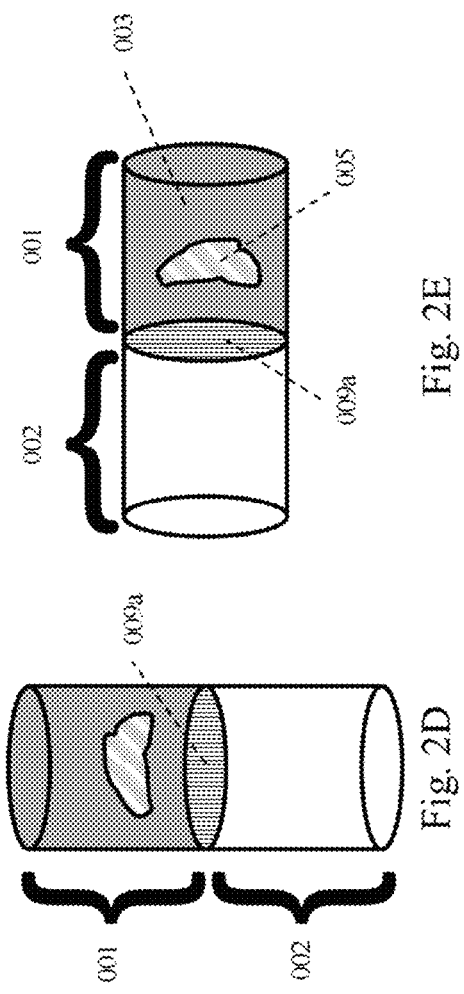

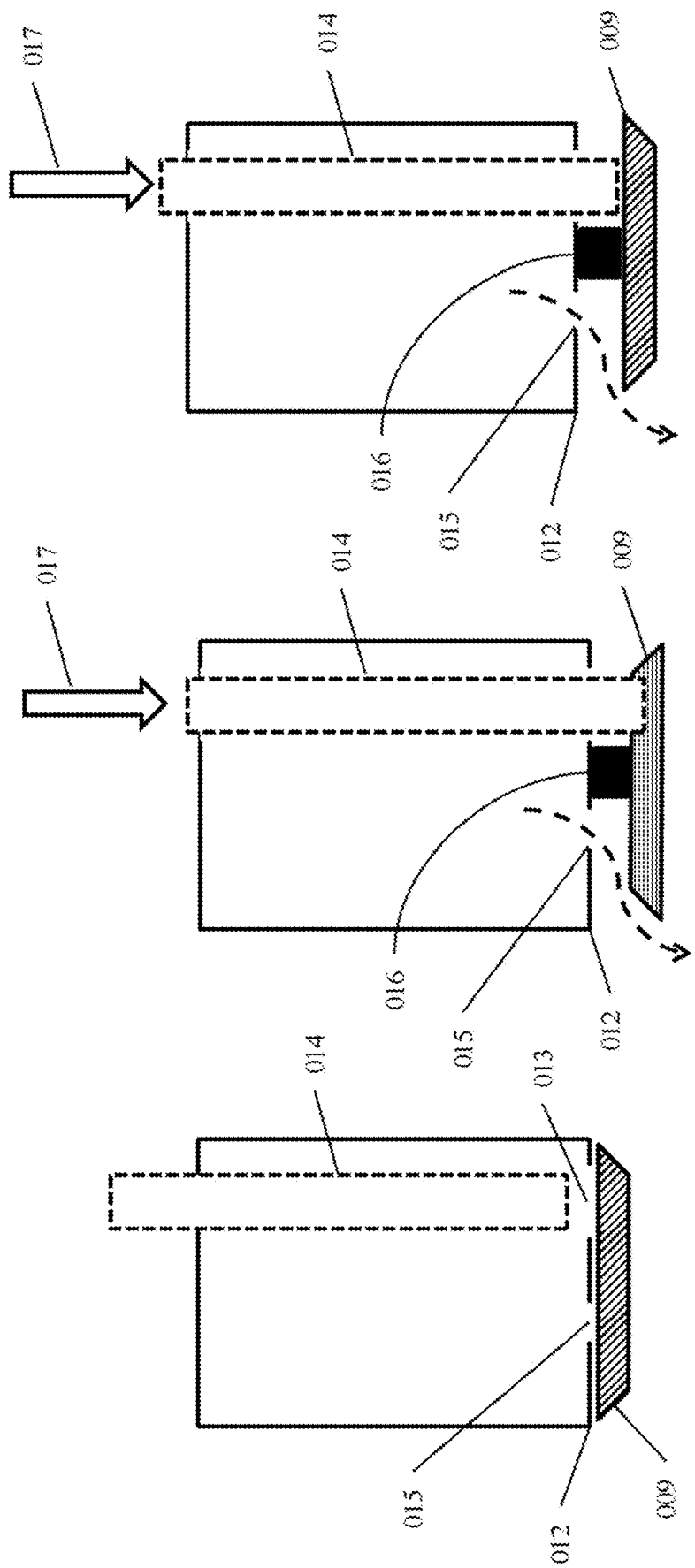

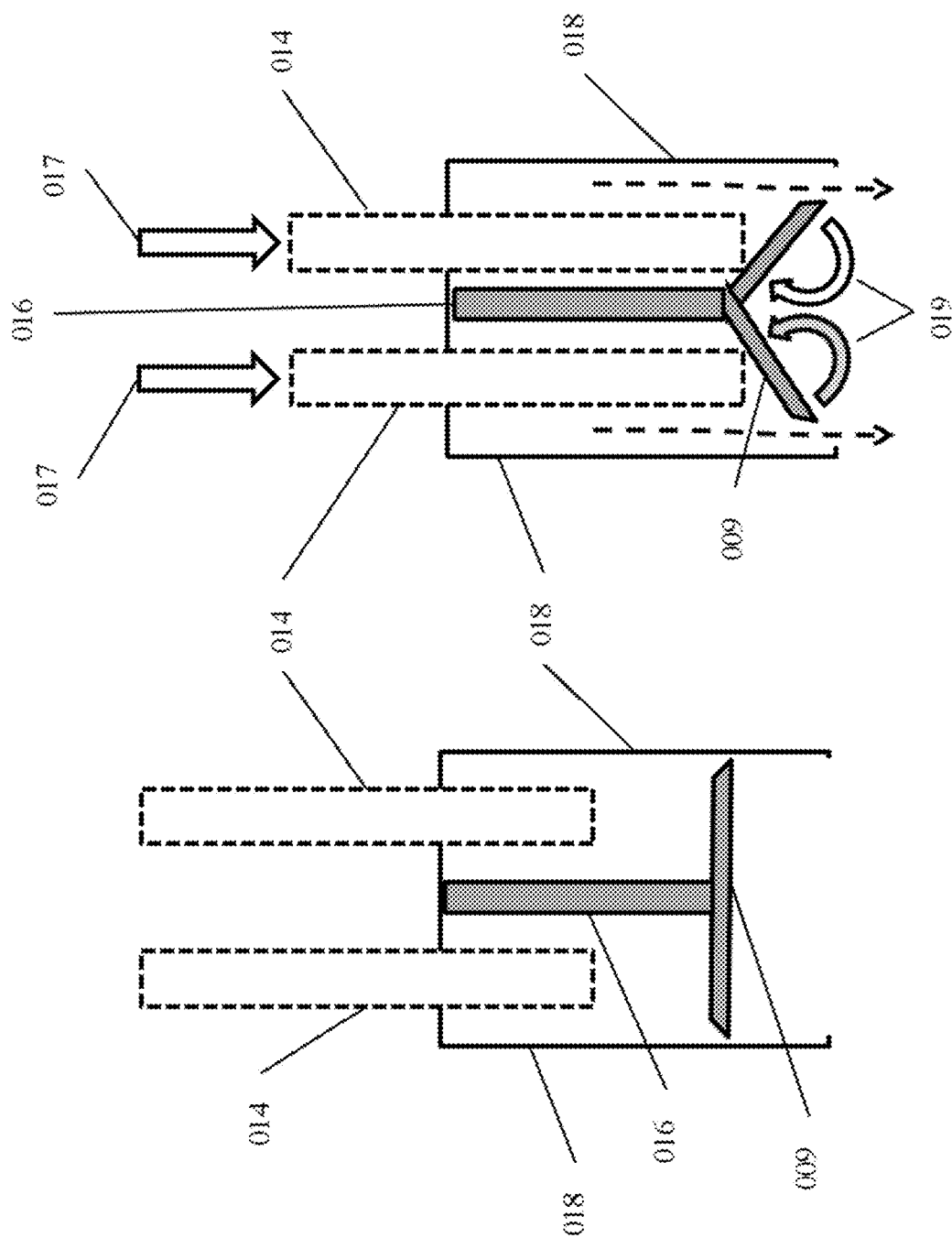

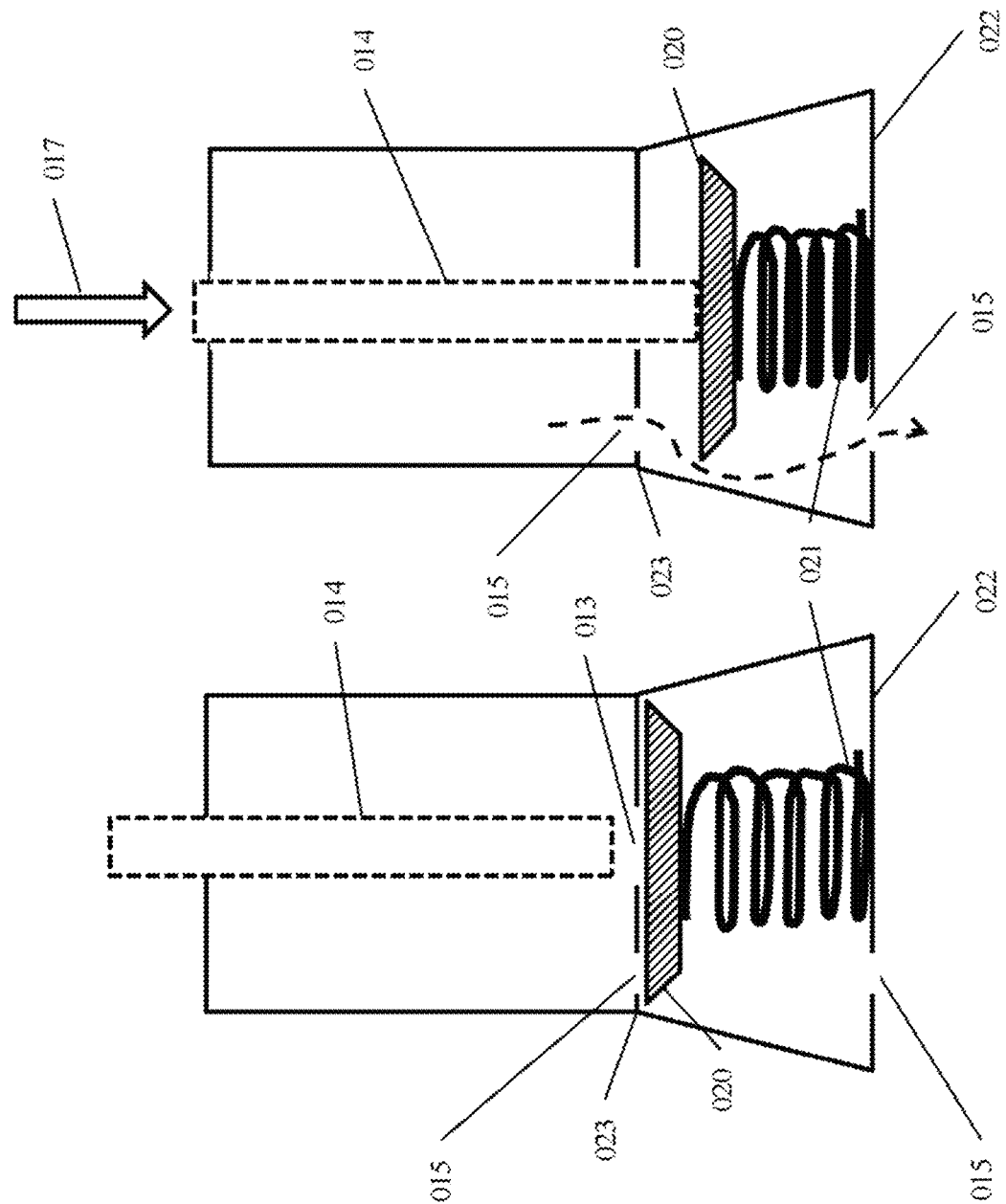

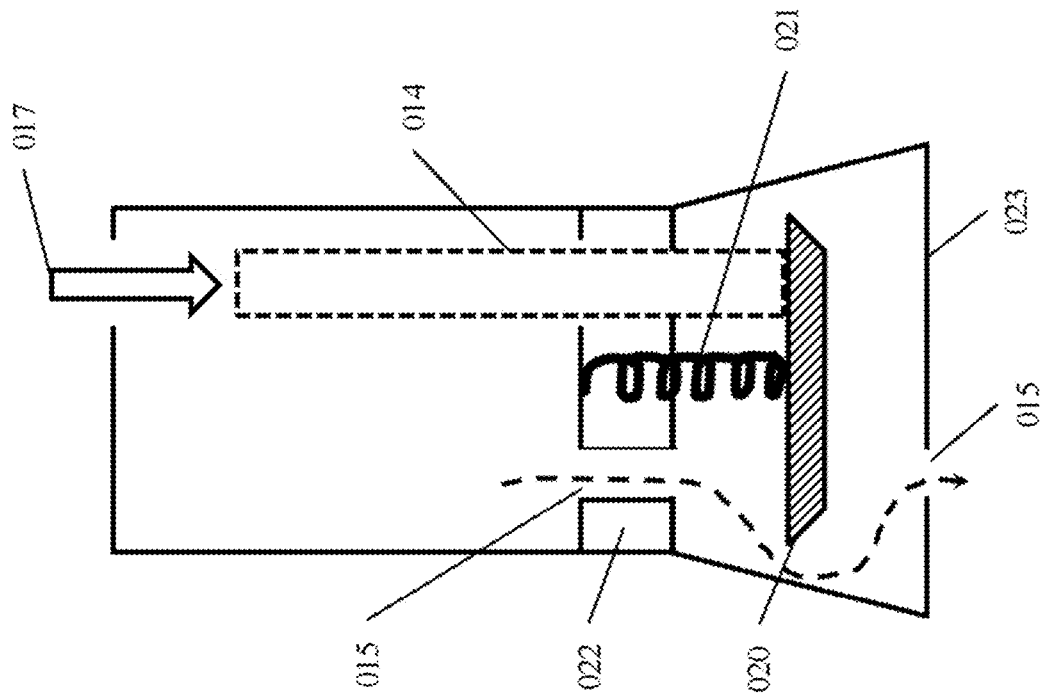
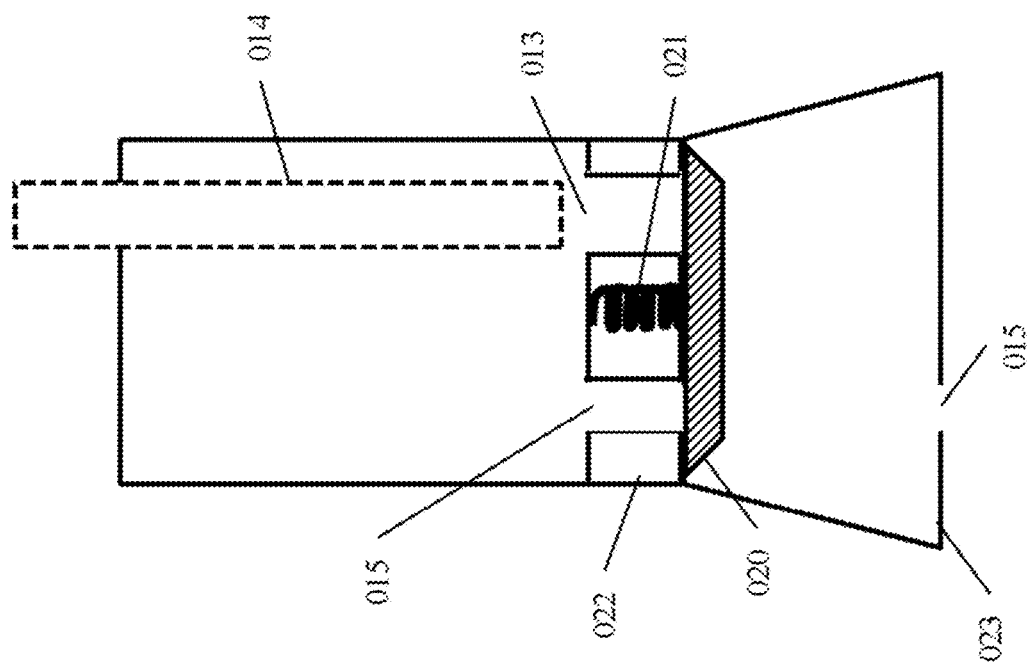
Fig. 5D
Fig. 5C

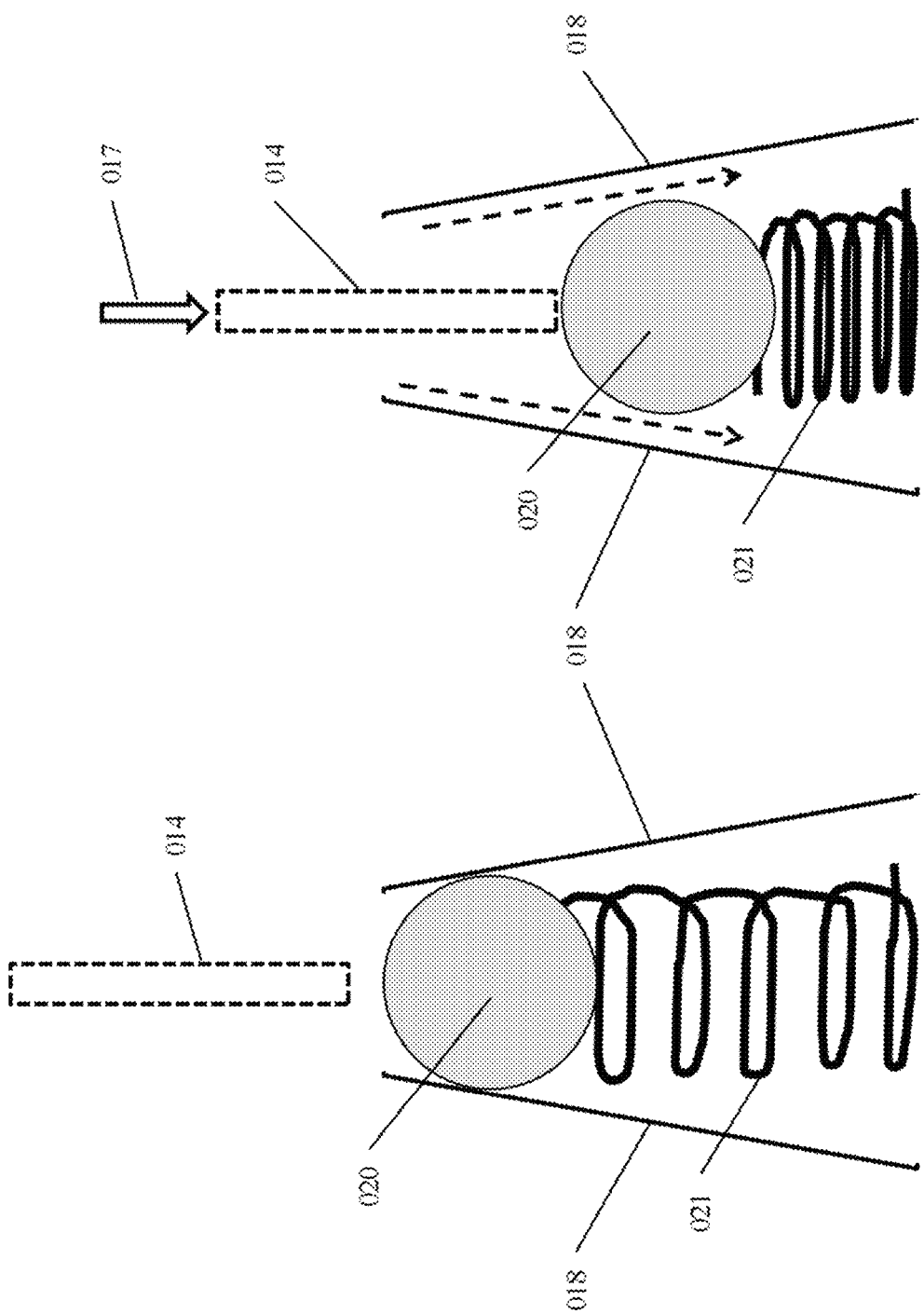

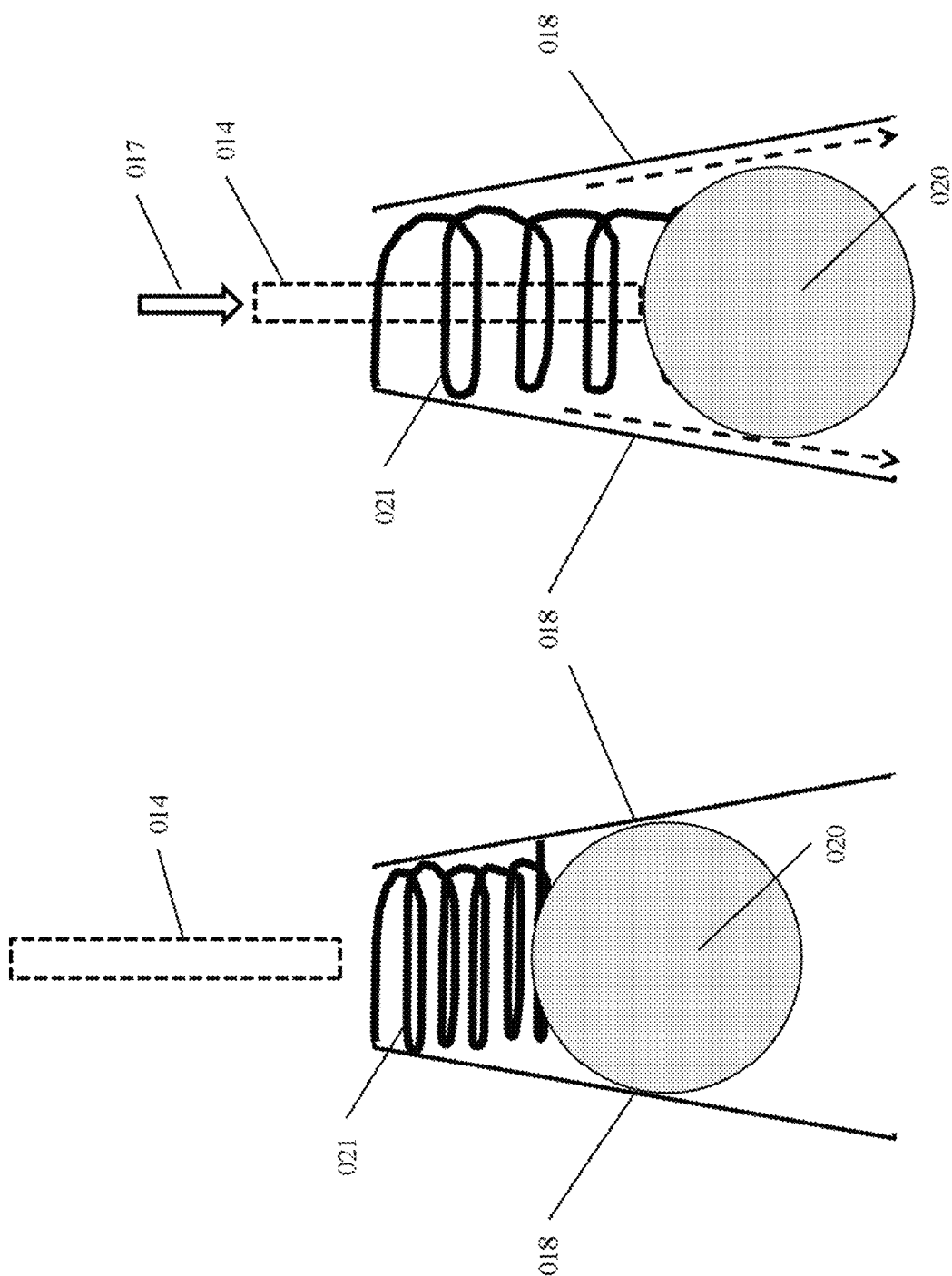

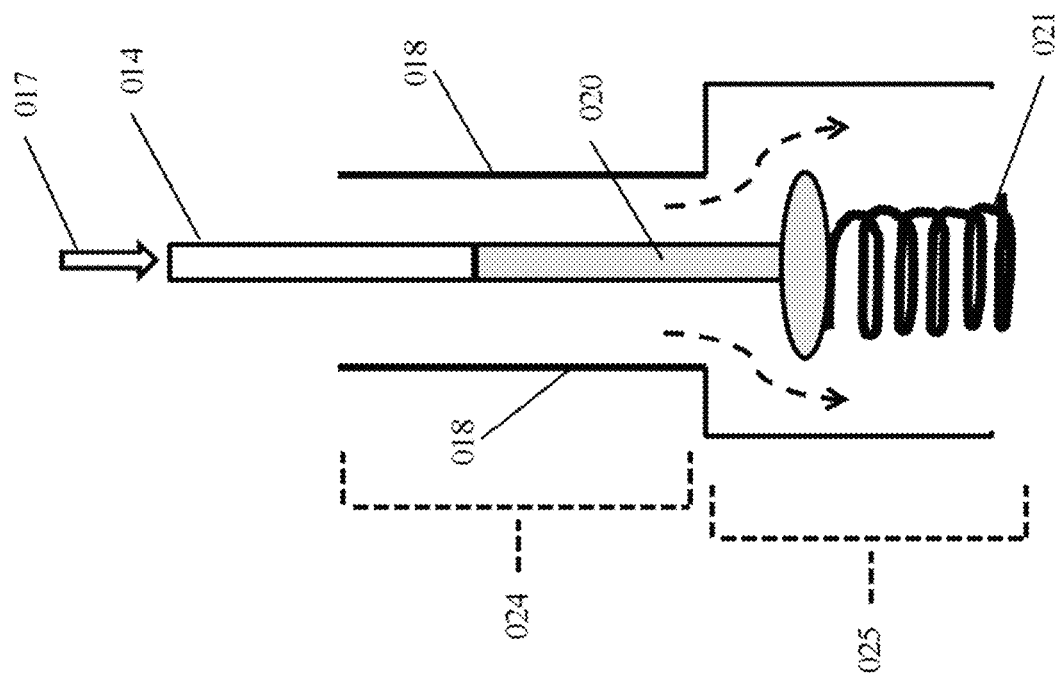
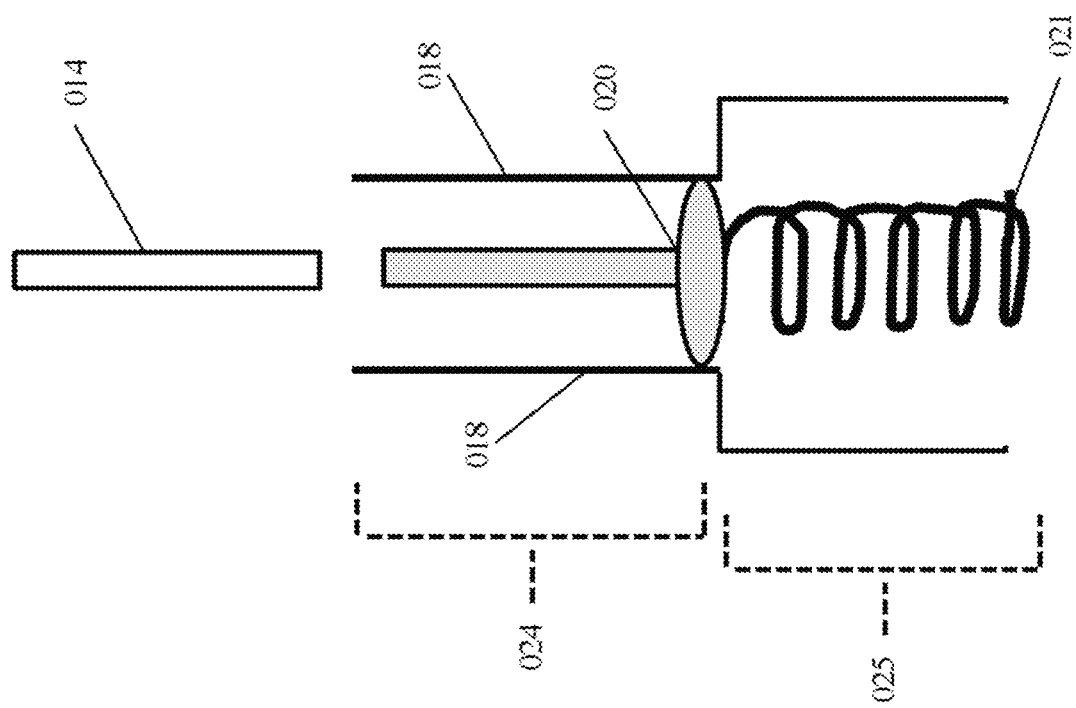

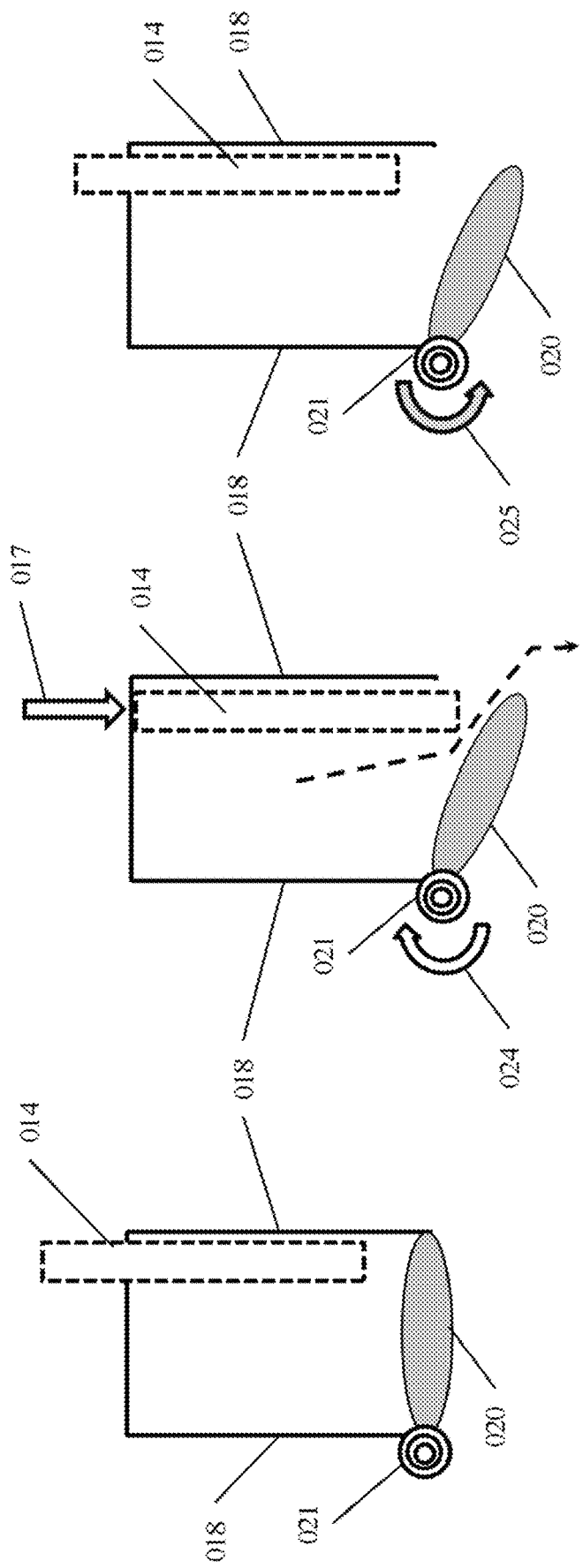

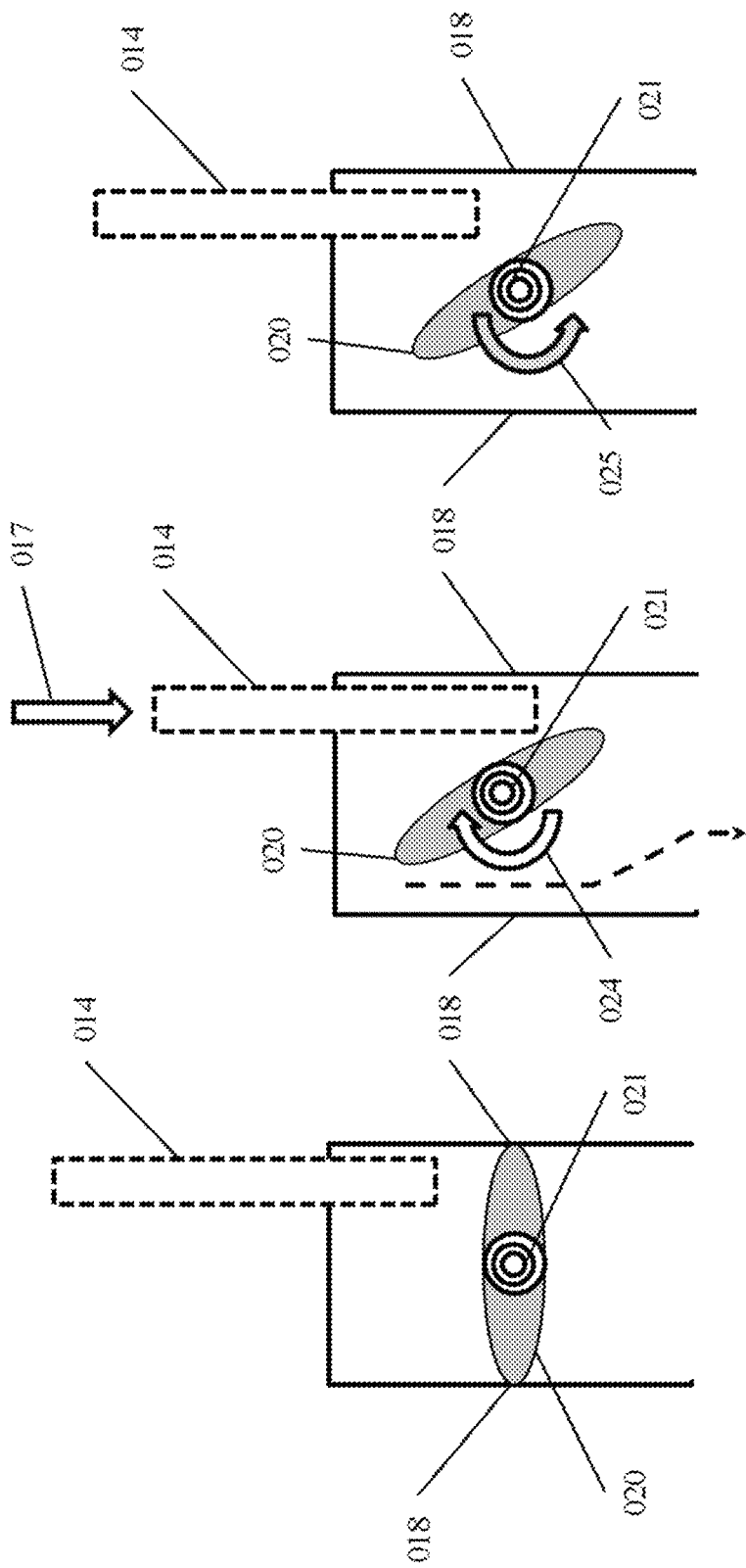

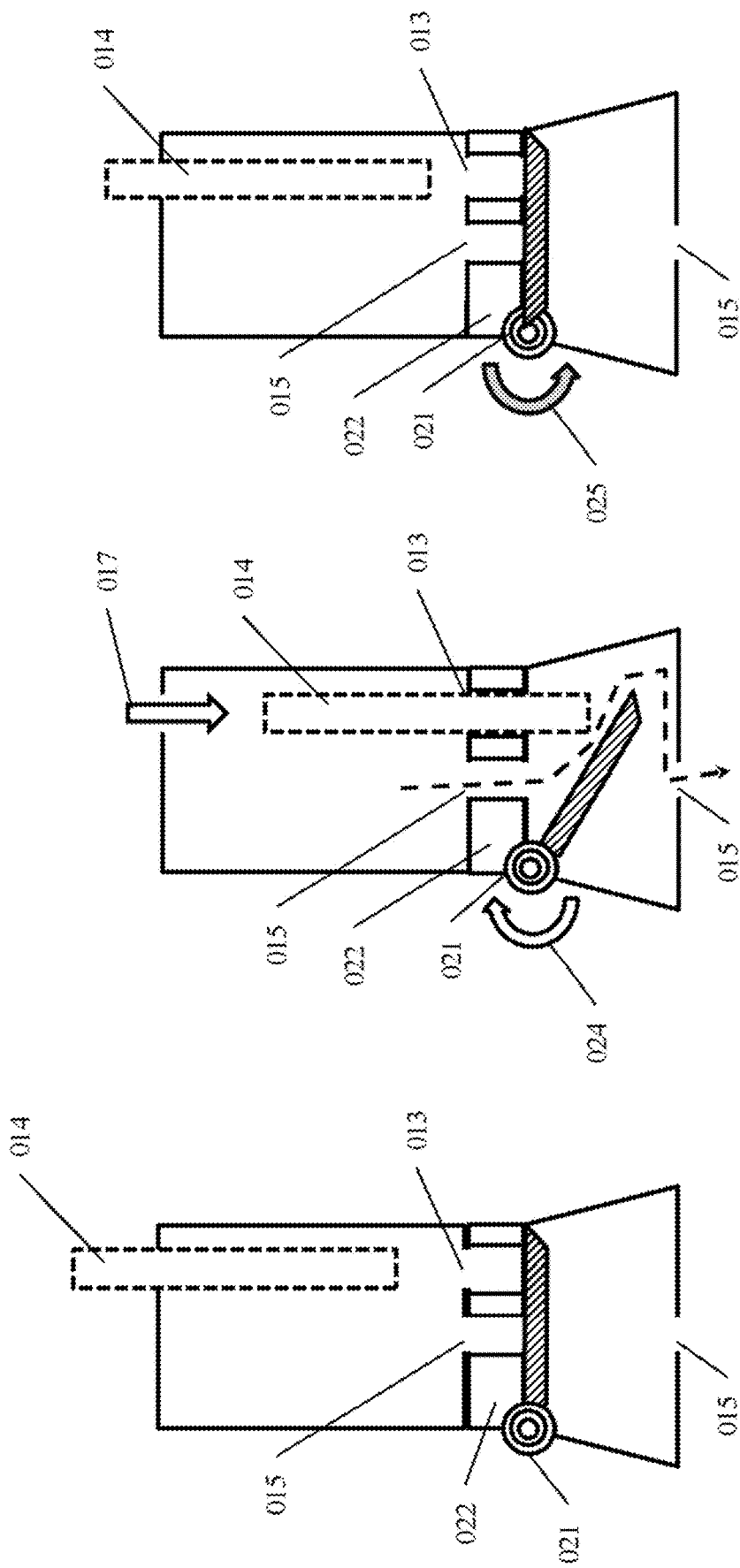

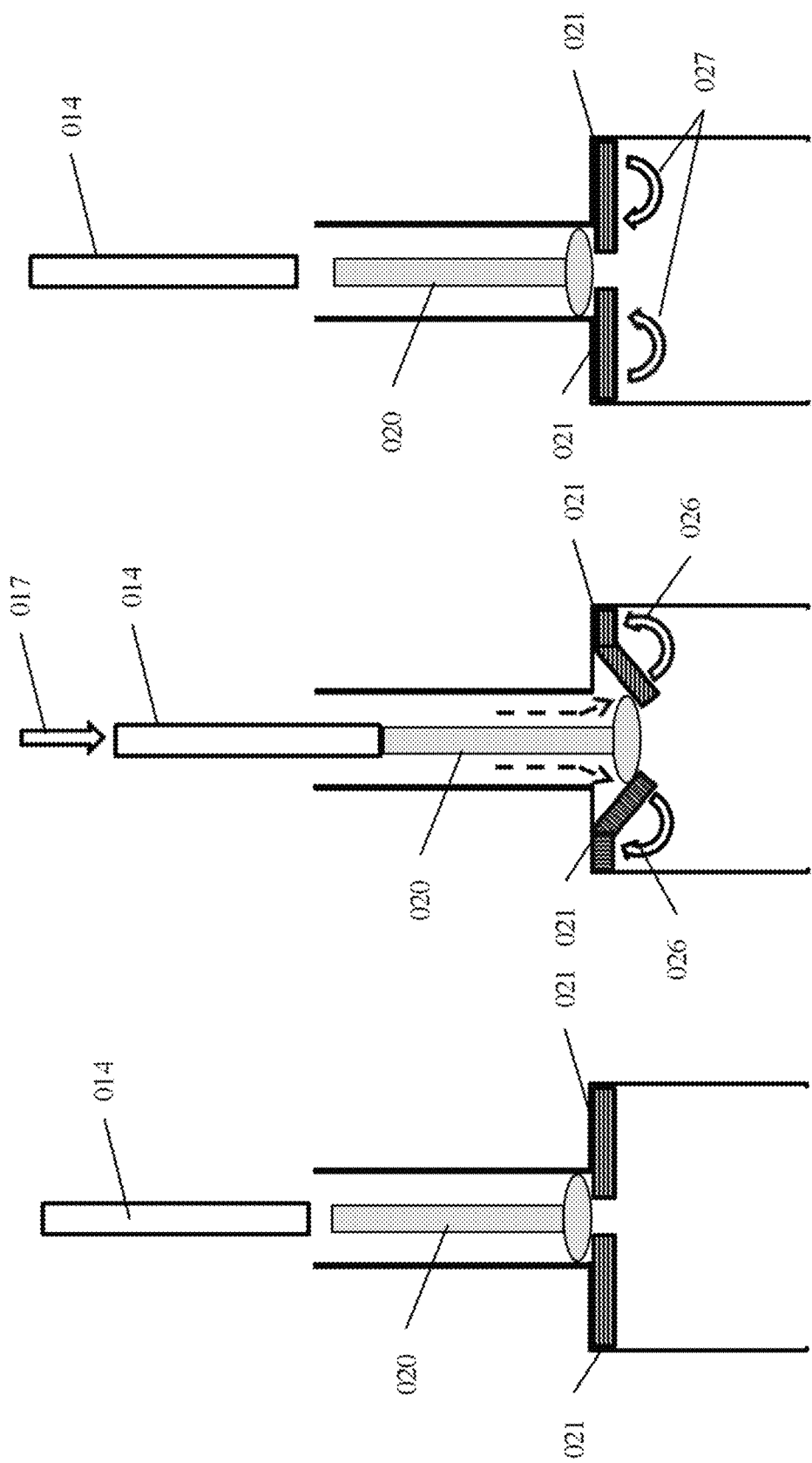

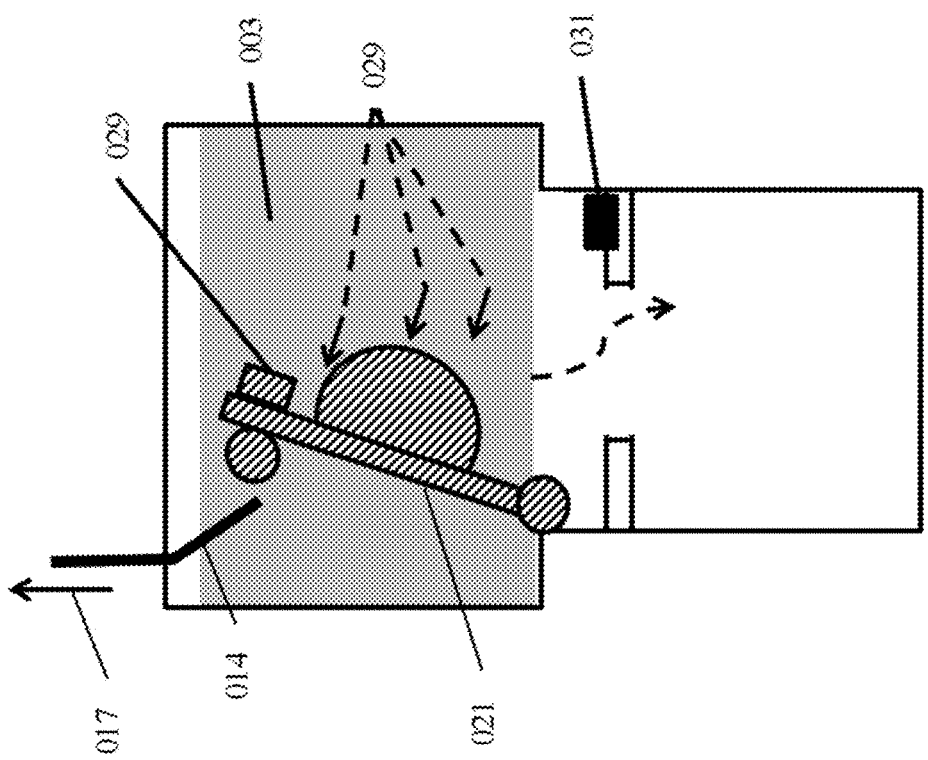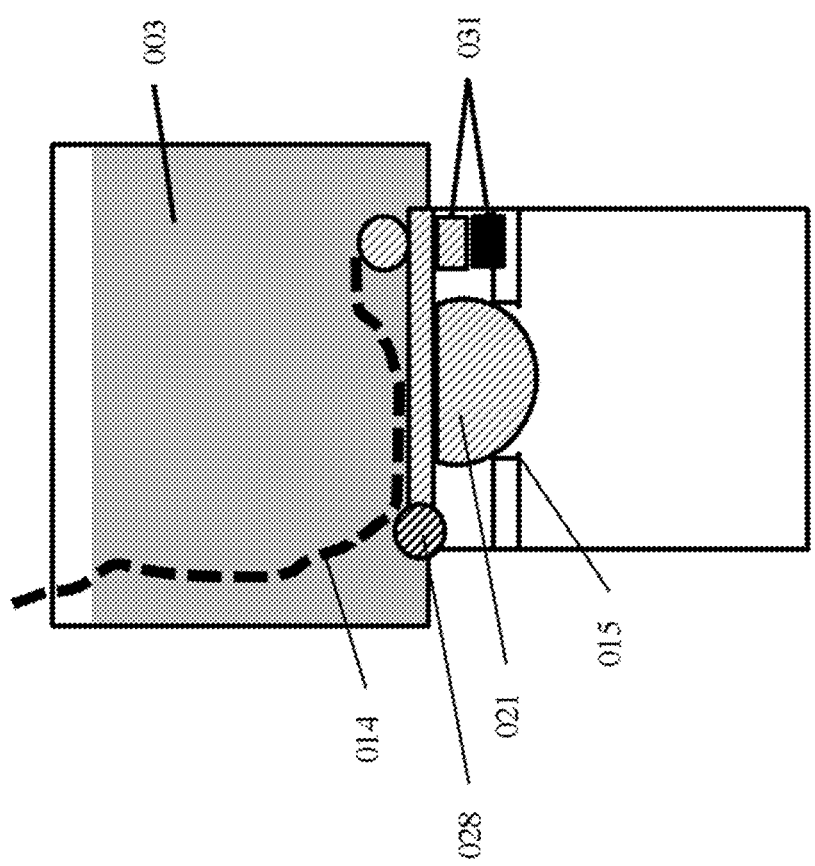
Fig. 10B
Fig. 10A

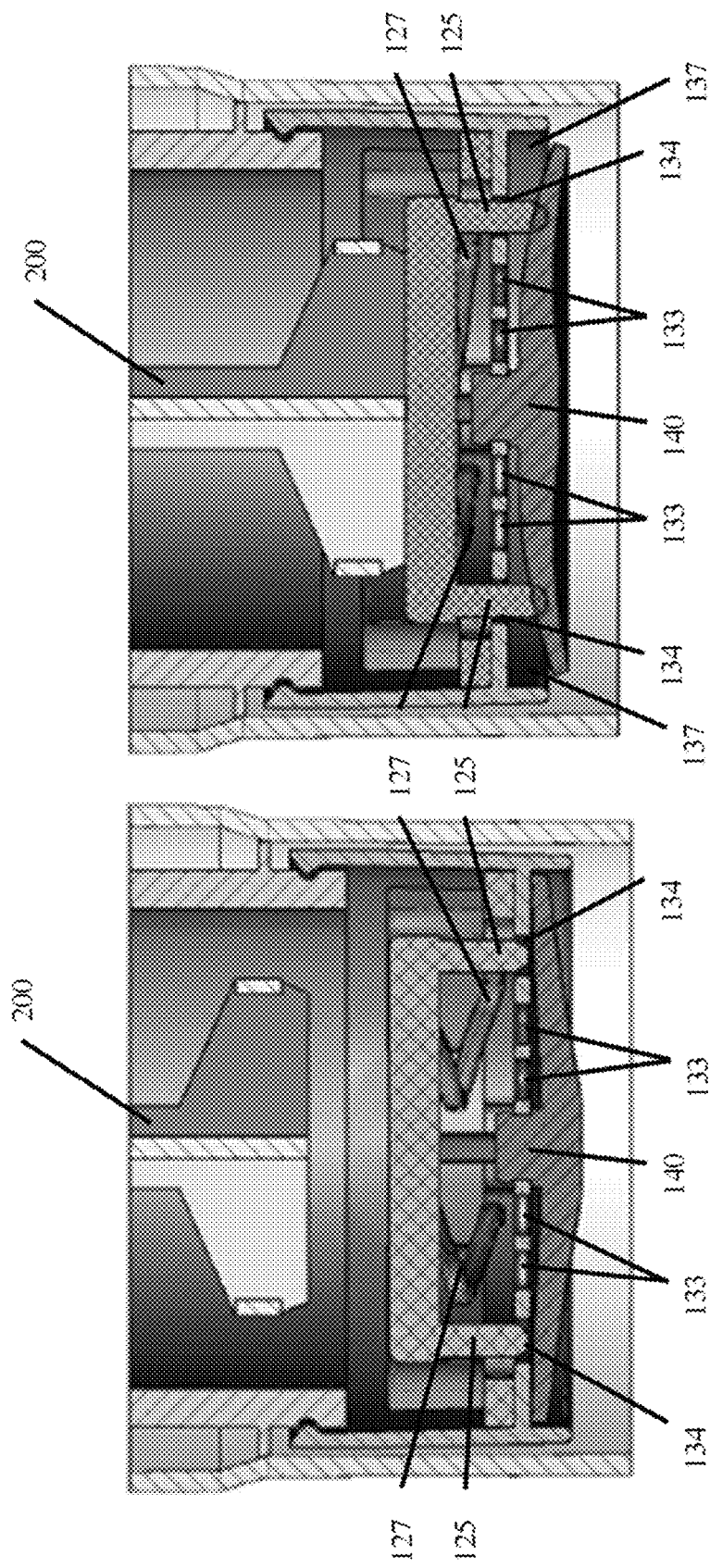

With lower fluid remaining, the effect of gravity drain is much less, therefore independent venting paths are needed for air exchange In slanted orientation, air channels may be obstructed by fluid. Due to several air exchange channels around the circumference, air exchange is still possible

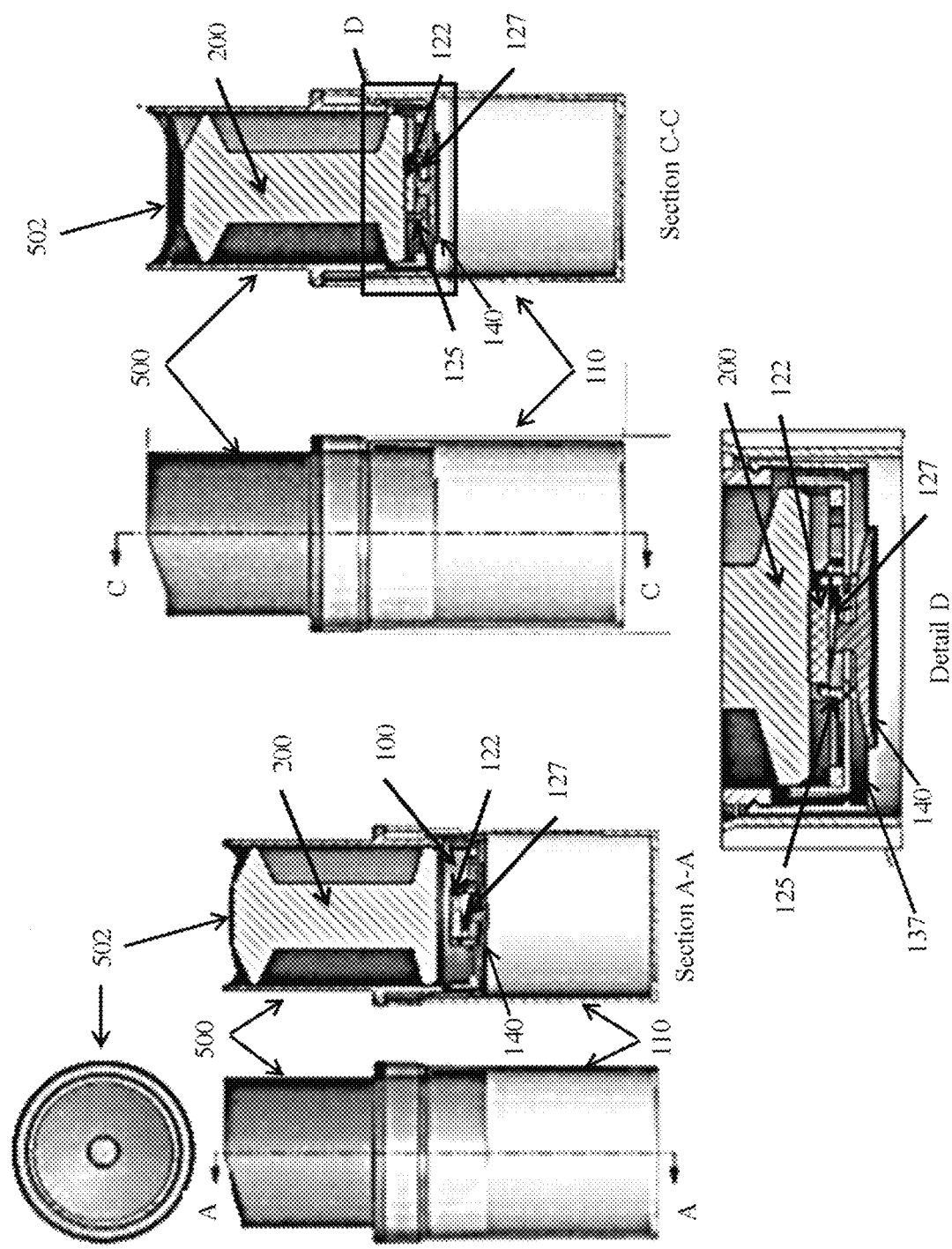

ASSEMBLY FOR STORING AND TRANSPORTING TISSUE SAMPLES IMMERSED IN A FLUID

CROSS-REFERENCE TO RELATED APPLICATION

This is a continuation of International Patent Application PCT/EP2016/053341, filed Feb. 17, 2016, which claims priority to and the benefit of both U.S. Provisional Patent Application No. 62/118,878, filed on Feb. 20, 2015, and U.S. Provisional Patent Application No. 62/165,616, filed on May 22, 2015. The contents of these related applications are incorporated by reference herein.

BACKGROUND

Field

The present disclosure relates to a sample collection system having an inversion protection feature, namely, an inversion protection cap for preventing backflow of a fluid.

Brief Discussion

Preservation of tissue removed by surgical procedures is a topic of great importance. After removal of a tissue sample from a subject, the tissue sample is often placed in a liquid that will suspend the metabolic activities of the cells. This process is commonly referred to as "fixation" and may be accomplished by several different types of liquids. Unfortunately, fixative solutions are quite often hazardous. For example, the most commonly-used fixative is 10% neutral buffered formalin (NBF). Formaldehyde—the main component of NBF—is a suspected carcinogen. Moreover, formaldehyde fumes can irritate eyes and mucous membranes, causing headaches, burning sensations in the throat, difficulty breathing and can trigger or aggravate asthma symptoms. Additionally some people have heightened sensitivity to formaldehyde and can suffer severe allergic reactions. Therefore handling a wetted, open container of formalin to insert a tissue specimen carries significant health risks—especially in close proximity to patients & patient treatment facilities.

WO2012/171529 discloses at least one solution to address the problem of workplace safety by hermetically sealing the formalin inside the specimen container and releasing it to submerge the specimen only once the container has been closed. This is achieved by use of two internal chambers—a clean, dry one for the specimen and a sealed one in the cap filled with formalin. Once the container is closed the seal can be broken from the outside by actuating an internal plunger, exchanging the formalin to the specimen chamber and vice versa exchanging the air from the specimen chamber to the cap. However this solution is dependent on gravity to keep the specimen submerged. If the container is oriented in anything but an upright position, the formalin is free to flow back into the cap—starving the specimen of liquid formalin. This situation is not easily detectable upon receipt, and the quality of the sample may be compromised if the sample is drying out. Thus, the containers described in WO2012/171529 must be kept in an upright position at all times, which is a serious risk to take with highly valuable patient samples.

Arrangements for storing and transporting tissue samples that both protect technicians from exposure to fixative solutions and permit storage and transport of the device in any orientation do not appear known.

SUMMARY

The present disclosure relates to an assembly for storing and transporting biological samples immersed in a fixative solution, the assembly containing a valve disposed between a cap prefilled with a fixative solution and container for holding the tissue sample. When assembled, the valve is adapted to allow fluid to flow from the cap into the container when the assembly is in an upright position, but prevents fluid exchange between the cap and the container when the assembly is in a substantially horizontal or inverted position. Preferably, the valve is adapted to default to a closed position, such that an external force is required to hold the valve in an open configuration that permits fluid exchange between the cap and the container and the valve automatically closes when the external force is removed.

In a first embodiment, the assembly comprises:
  a cap comprising a first chamber prefilled with a volume of a fixative solution;
  a sample container comprising a second chamber for holding the biological sample; and
  a valve situated between the first chamber and the second chamber and adapted to switch between a closed configuration and an open configuration, wherein:
    when the valve is in the open configuration, one or more channel(s) is formed between the first and second chamber permitting fixative solution to flow from the first chamber to the second chamber, and allow air to be vented in exchange;
    when the valve is in the closed configuration, the valve creates a barrier between the first chamber and the second chamber that prevents flow of the fixative solution from the second chamber to the first chamber;
    the valve is configured to switch from the closed configuration to the open configuration upon application of a first force; and
    the valve is configured to default back to the closed configuration upon removal of the first force; and
  an actuator moveable between a disengaged position and an engaged position, wherein:
    application of a second force on the actuator moves the actuator from the disengaged position to the engaged position and holds the actuator in the engaged position, thereby causing the actuator to apply the first force to the valve; and
    removal of the second force from the actuator releases the first force from the valve.

In an example, the valve of the first embodiment includes a material having an inherent resiliency that forms at least part of the barrier between the first and second chambers. The first force causes the material to deform, which creates a channel between the first and second chambers through which fluid can flow. When the first force is removed, the inherent resiliency of the material causes the material to return to its original shape, which closes the channel, thereby preventing backflow of fluid from the second chamber to the first chamber regardless of how the assembly is oriented. The actuator in this embodiment may include rigid members that can be placed in contact with a surface of the material to cause deformation. Thus, for example, application of the second force to the actuator moves the rigid members into contact with the material having inherent resiliency and causing the material to deform, thereby putting the valve in the open configuration. The movement of the rigid members toward the material may also generate a third force that acts upon the actuator counteracting the second force, such that when the second force is removed, the third force causes the rigid members to move away from the material. For example, a resilient mechanism placed in contact with the actuator is bent, compressed, stretched, twisted, or rotated when the actuator is moved toward the material, which introduces tension into the resilient mechanism. The tension built into the resilient mechanism exerts the third force on the actuator so that, when the second force is removed, the actuator is forced away from the material and the material is allowed to return to its original shape. Additionally or alternatively, the third force may be exerted on the actuator by the material having inherent resiliency. Deforming the material introduces tension into the system, the tension tending to return the material to its original shape. Thus, when the second force is applied to the actuator and the rigid members deform the material, a third force is applied on the actuator by the tension accumulating in the material. As long as the second force is maintained, the tension will be retained in the material. When the second force is removed, however, the tension is released, causing the material to return to its original shape and forcing the actuator away from the material. Examples of valves incorporating such material having inherent resiliency include, for example, umbrella valves and duckbill valves.

In another example of the first embodiment, the valve comprises:
- a valve wall defining an aperture that connects the first chamber and the second chamber, and
- a seal configured such that:
  - when the valve is in the closed configuration, the seal is in contact with the valve wall to create the barrier between the first chamber and the second chamber; and
  - application of the first force to the valve causes the seal to lose contact with the valve wall to create the channel; and
  - the seal automatically returns in contact with the valve wall when the first force is removed.

When the seal is in contact with the valve wall, it creates a barrier impervious to the fluid contained in the cap. The seal should be arranged in the aperture such that, when the actuator is moved to the engaged position, the seal loses contact with the valve wall to create a channel through which the fluid can flow. In one arrangement, the seal is placed in the aperture while in contact with a resilient mechanism. When the first force is applied to valve, tension is introduced into the resilient mechanism (such as by stretching, compression, twisting, or bending, depending on the arrangement), and the seal moves from a first position to a second position inside of the aperture. The aperture is sized such that, when the seal is in the first position, an outer edge of the seal is in contact with the valve wall around the entire inner perimeter of the aperture to prevent fluid from flowing through the aperture (closed configuration in this embodiment), and when the seal is in the second position, there is a gap between at least a portion of the outer edge of the seal and the valve wall, the gap creating a channel through which fluid can flow from the first chamber to the second chamber (the open configuration in this embodiment). When the first force is removed, the tension of the resilient mechanism is released, thereby forcing the seal back to the closed configuration.

In a second embodiment, the assembly comprises:
- a cap comprising a first chamber prefilled with a volume of a fixative solution;
- a sample container comprising a second chamber for holding the biological sample; and
- a valve situated between the first chamber and the second chamber and adapted to switch between a closed configuration and an open configuration, wherein:
  - when the valve is in the open configuration, one or more channel(s) is formed between the first and second chamber permitting fixative solution to flow from the first chamber to the second chamber, and allow air to be vented in exchange;
  - when the valve is in the closed configuration, the valve creates a barrier between the first chamber and the second chamber that prevents flow of the fixative solution from the second chamber to the first chamber;
  - the valve is configured to switch from the closed configuration to the open configuration upon application of a first force; and
  - the valve is configured to default back to the closed configuration upon removal of the first force; and
- an actuator moveable between a disengaged position and an engaged position, wherein:
  - application of a second force to the actuator causes movement of the actuator from the disengaged position to the engaged position, thereby applying the first force to the valve; and
  - movement of the actuator from the engaged position to the disengaged position releases the first force from the valve.

In this embodiment, movement of the actuator from the engaged position to the disengaged position can happen automatically upon removal of the second force (such as the configurations discussed in the first embodiment), or can require the application of an additional external force. For example, the user can apply the second force to the actuator to until the actuator moves into the engaged position. The actuator is then adapted to remain in the engaged position without application of an external force by the user (such as by use of a retention mechanism or by a friction fit) until the user applies an additional external force that causes the actuator to move from the engaged position back to the disengaged position, such that the valve switches to the closed configuration.

In a third embodiment, the assembly comprises:
- a cap comprising a first chamber prefilled with a volume of a fixative solution;
- a sample container comprising a second chamber for holding the biological sample; and
- a valve situated between the first chamber and the second chamber and adapted to switch between a closed configuration and an open configuration, wherein:
  - when the valve is in the open configuration, one or more channel(s) is formed between the first and second chamber permitting fixative solution to flow from the first chamber to the second chamber, and allow air to be vented in exchange;
  - when the valve is in the closed configuration, the valve creates a barrier between the first chamber and the second chamber that prevents flow of the fixative solution from the second chamber to the first chamber;
  - the valve is configured to switch from the closed configuration to the open configuration upon application of a fluid pressure exceeding a threshold; and the valve is configured to default back to the closed configuration upon reduction of the fluid pressure to below the threshold; and an actuator adapted to increase the fluid pressure above the threshold.

In an example, the actuator may be fit with a plunger in mechanical communication with the volume of fixative solution in the cap. While the actuator is at rest, the fluid pressure of the fixative solution on the valve is below the threshold.

Movement of the actuator in a direction that causes the volume of fixative to flow toward the valve increases the fluid pressure on the valve until the threshold is exceeded. The increased pressure forces a channel in the valve to open, thereby placing the valve in the open configuration. When the actuator stops moving or the fluid has completely flowed into the container, the fluid pressure on the valve reduces, and the channel in the valve automatically closes, thereby returning the valve to the closed configuration. Examples of valves useful for such an arrangement include duckbill valves and check valves.

In a fourth embodiment, a valve assembly is provided for use in the assembly for storing and/or transporting the biological sample, the valve assembly comprising:

a valve having a valve top surface, a valve bottom surface, and a valve periphery, wherein the valve is constructed such that application of a force to the valve top surface near the valve periphery causes the valve periphery to deform from an original configuration by flexing, and wherein the valve returns to the original configuration upon removal of the force.

a valve actuator sized to fit over the top surface of the valve, the valve actuator comprising:

an outer frame;

a support structure having a support top surface, a support bottom surface, and at least one arm disposed on the support bottom surface and projecting toward the top surface of the valve when the valve actuator is disposed over the top of the valve surface; and at least one resilient mechanism having a first end attached to the outer frame and a second end attached to on the support structure.

In another embodiment, the support top surface has a plunger that can be pressed to move the control assembly from a first to a second position such that the spring is compressed from the first relaxed state and the arm pushes upon and flexes the valve top surface to enable the fluid to flow through drain apertures.

In one embodiment, the valve assembly can have a valve actuator having an outer frame, a support structure with a support top surface, a support bottom surface, and a plurality of arms disposed on the support bottom surface and which project outwardly and away from the support structure. The outer frame may comprise at least one frame locking tab and a valve housing may be provided comprising at least one housing locking tab complementary to the frame locking tab. The frame locking tab and the housing locking tab prevent the valve actuator flexure from moving (i.e. rotating) in the valve housing. For example, the outer frame may comprise two, three, or four frame locking tabs and the valve housing may comprise two, three, or four housing locking tabs. The valve assembly can also contain a plurality of springs having a first and a second end where the first end of each spring is attached to the outer frame and the second end of each spring is attached to the support structure. A valve housing comprising a base, a sidewall, a plurality of drain apertures, a plurality of arm apertures, and a stem opening disposed on the base may also be provided. Additionally a valve with a valve top surface, a valve bottom surface and a valve stem can be disposed on the valve top surface, wherein the valve stem has a bulbous stem end. The valve actuator can be disposed inside the valve housing, and the valve disposed on the base such that the valve top surface interfaces with a base bottom surface and the base is positioned between the valve actuator and the valve. The bulbous stem end of the valve stem can pass through the stem opening of the support structure with the bulbous stem end securing the valve stem to the stem opening. The support top surface of the support structure may also be in contact with a plunger on the support top surface which when presses the assembly is moved to a second position where the plurality of springs are compressed and the valve top surface is pushed away from the base bottom surface so the fluid can flow through the drain apertures.

In operation, the valve assembly is disposed into a container having a top portion and a bottom portion, the top portion for storing a fixative solution and the bottom portion for storing a biological sample. The valve is sized such that the valve periphery fits snugly against an inner surface of the container or a valve housing adapted to securely fit in either the top portion or the bottom portion. The snug fit between the valve periphery and the container or valve housing creates a barrier that prevents fluid flow between the top and bottom portion of the container. A plunger or other device that facilitates user-initiated actuation of the actuator is disposed in the container in an arrangement that allows a user to interact with it. The user applies activates the device, which applies a force to the top surface of the support structure. The force applied to the top surface introduces tension into the resilient mechanism and moves the at least one arm in a manner that applies a force on the top surface of the valve. The force applied on the top surface of the valve causes the valve to flex away from the inner surface of the container, creating a channel between the valve and the inner surface of the container through which fluid can flow. When the operator removes force from the plunger, the tension in the resilient mechanism is released, causing the at least one arm to move away from the top surface of the valve and releasing the force on the top surface of the valve, whereupon the valve periphery automatically returns to the original configuration to close the channel.

In some embodiments, the valve assembly is a part of a system for storing and/or transporting a biological sample, the system comprising: (a) the valve assembly, (b) a cap prefilled with a preservative fluid and optionally containing a primary seal separating the fixative fluid from the valve when assembled, and (c) a sample collection container.

In some embodiments, the valve assembly caps the sample collection container or the prefilled cap, such that the valve is disposed inside the sample collection container or the cap. For example, the valve assembly is screwed or snapped onto the container or the cap.

In some embodiments, the cap may further comprise a plunger, a seal, and the fluid. The cap may be removeably attached to the valve assembly. The seal can seal the plunger and the fluid inside the cap.

When the assembly is in a first position, the spring is in a relaxed state. When the plunger is pressed upon the support top surface, the assembly is moved from the first position to a second position. When the assembly is in the second position, the spring is compressed and the arm pushes upon the valve top surface to flex the valve such that the fluid flows through the drain apertures and contacts a sample disposed in the container.

In some embodiments, the fluid is a preservative fluid. In other embodiments, the fixation procedures utilize cross-linking agents, like aldehyde-based fixative solutions. For example, the aldehyde-based fixative solutions is formalin. Another example of the fixative solution may be an aqueous formaldehyde solution that includes sodium phosphates, formulated to provide buffering to pH 7.2-7.6 and an approximately isotonic solution. In another embodiment, the fluid may comprise bis-maleic anhydrides, such as those found in U.S. Pat. No. 8,658,109. Other exemplary fluids may include, but are not limited to coagulants such as mercuric chloride, picric acid, or zinc sulfate, noncoagulant fixatives such as glyoxal or glutaraldehyde, acetone, acetic acid, Bouin's fluid, or other organic solvents.

In some embodiments, the sample is collected and placed inside the sample collection container. The sample can be a blood, urine, tissue, cell or mucous sample. For example, the sample can be portion of an abnormal tissue mass for biopsies, or cervical cells for pap smears.

Preferably, the sample collection system is fume-safe, i.e. does not emit fluid fumes.

In alternative embodiments, the sample collection system may be coupled to sampling device, such as a sampling device for gathering cervical tissue, a syringe for gathering blood, or a biopsy tool for gathering tissue. For example, the sampling device collects a sample, which is then deposited into the sample collection container. In another example, the sample may be collected on a portion of the sampling device, the sample-containing portion is then placed in the container and separated from the sampling device, thereby leaving the sample-containing portion inside the container. Exemplary sampling devices can be found in U.S. Publication No. 2014/01850165, the disclosures of which are incorporated herein.

In other embodiments, the system further comprises a cassette. The sample can be placed in the cassette, and the cassette can be disposed inside the sample collection container. Preferably, the collection container is sufficiently sized to allow for full insertion of standard histology tissue cassettes.

In some embodiments, the sample collection container may come in a varying shapes and dimensions. Exemplary shapes of the container include, but are not limited to, cylinders and rectangular prisms. The container may also have a volume ranging from about 10 ml to 30 ml, or about 30 ml to 50 ml, or about 50 ml to 70 ml, or about 70 ml to 100 ml. For example, the container may be a cylinder having a diameter of about 2 cm and a volume capacity of about 60 ml. As another example, the container may be a square or rectangular tube having a volume capacity of 20 ml.

In other embodiments, the sample collection system may further comprise a carrier assembly configured to retain or hold the sample collection container and a monitoring system comprising a data logging device and at least one sensor configured to obtain, store or transmit one or both of time and temperature information about the sample or fluid in the container when the container is placed in the carrier assembly and transported to a laboratory. In still further embodiments, the system comprises a transport container comprising an internal holding compartment for transporting the sampled collection container, carrier assembly and monitoring system. The transport container may be configured to maintain a temperature of the internal holding chamber at a temperature of between about 0° C. to about 20° C. for a sufficient amount of time to allow for delivery of the sample to a testing facility. For example, the transport container can maintain a temperature of 5° C. for at least 1 hour.

Exemplary transporter containers or assemblies can include, but are not limited to, packaging, a bottle, a vial, or other object used to hold liquid media and at least one sample. The transporter systems can include machine-readable code (e.g., optical symbology, magnetic pattern or electromagnetic, or electrostatic signal having information content) that may relate to sample identity, patient information, sample origin, sample chain of custody, instructions for processing samples, information regarding the characteristics of samples, test results for samples, images of samples, or other information associated with the tissue sample.

In some embodiments, the transport assembly containing the processed sample may be transported from a first location to a second location. For example, the first location may be a location off-site from a testing facility, such as a doctor's office. The transport assembly is then sent to the testing facility for analysis. In another example, the first location may on-site of a testing facility, such a sample collection room. The transport assembly is then sent to a separate room in the testing facility for further processing.

Alternate embodiments may feature a gripping component disposed on the sample collection container. For example, the gripping component is disposed on an external surface of the container. The gripping component can reduce the risk of dropping the container as it is being handled. Moreover, the gripping component can hold the container in place.

In some embodiments, the gripping component comprises an indentation and the carrier assembly comprises a protrusion such that the indentation and the protrusion matingly lock the sample collection container in the carrier assembly to prevent displacement of the sample collection container. In other embodiments, the gripping component comprises a protrusion and the carrier assembly comprises an indentation such that the protrusion and the indentation matingly lock the sample collection container in the carrier assembly to prevent displacement of the sample collection container.

In preferred embodiments, in the gripping component comprises a notched or patterned surface, such as a knurled surface. The knurled surface can be an annular ring pattern, a linear knurl pattern, or a diamond knurl pattern.

In some embodiments, the sample collection container may further comprise a temperature sensor for measuring and transmitting a temperature of the fluid contained therein to the monitoring system. In other embodiments, the sample collection container further comprises a radio frequency identification (RFID) tag and the monitoring system further comprises an RFID reader.

In some embodiments, the valve further comprises a valve stem having a bulbous stem end, wherein the valve stem is disposed on the valve top surface. In one embodiment, the valve is attached to the valve housing via the bulbous stem end, wherein the bulbous stem end secures the valve stem to the valve housing. In another embodiment, the valve is attached to the support structure of the valve actuator flexure via the bulbous stem end, wherein the bulbous stem end secures the valve stem to the support structure. In still another embodiment, the valve is attached to a plunger via the bulbous stem end, wherein the bulbous stem end secures the valve stem to the plunger.

The plurality of arms may be disposed on the support bottom surface. In some embodiments, the plurality of arms project outwardly and away from the support structure. In other embodiments, the plurality of arms perpendicularly project downwardly from the support structure.

In some embodiments, each spring of the plurality of springs comprises a first end and a second end. In some embodiments, the first end of each spring may be attached to the outer frame. For example, the first end of each spring may be attached to an inner edge of the outer frame. In some embodiments, the second end of each spring may be attached to the support structure. For example, the second end of each spring may be attached to a periphery or the support bottom surface of the support structure.

In some embodiments, the valve is generally concaved when the assembly is in the first position. In other embodiments, the valve is generally convex when the assembly is in the second position.

In some embodiments, the plurality of arms is aligned with the plurality of arm apertures. In some embodiments, the number of arms is equal to the number of arm apertures. In some embodiments, the plurality of arms comprises four arms. In other embodiments, the plurality of arms comprises three arms. In still other embodiments, the plurality of arms comprises two arms.

Features as described herein are applicable to any embodiment of the assembly.

In some embodiments, the valve actuator flexure is constructed from a flexible material. In other embodiments, the valve actuator flexure is constructed from an elastomeric material. In some embodiments, the outer frame of the valve actuator flexure is generally ring-shaped. In other embodiments, the outer frame of the valve actuator flexure may be polygonal in shape.

In some embodiments, the valve is constructed from a flexible material. In other embodiments, the valve is constructed from an elastomeric material. In some embodiments, the valve is generally disc-shaped. In other embodiments, the valve is an umbrella valve. While in still other embodiments the valve can be a duckbill or a check-valve.

In some embodiments, the outer frame further comprises at least one frame locking tab. In some embodiments, the valve housing comprises at least one housing locking tab complementary to the frame locking tab. The frame locking tab and the housing locking tab prevent the valve actuator flexure from moving (i.e. rotating) in the valve housing. For example, the outer frame may comprise two, three, or four frame locking tabs. For example, the valve housing may comprise two, three, or four housing locking tabs.

In some embodiments, a plurality of air channels is disposed at or near the sidewall of the valve housing. For example, the number of air channels is two, three, or four air channels. In some embodiments, at least one air channel is disposed at or near the sidewall of the valve housing. The air channels allow for air and fluid exchange. For example, the fluid drains into the container until pressure in a cap is less than atmospheric pressure. This will stop the flow of fluid and require air exchange. The air in the container will through the air channels and into the cap to increase the pressure, thereby allowing for the fluid to flow again.

In another example, when the fluid level in the cap is low, the effect of gravity on the fluid draining is much less; therefore, the air channels are needed for air exchange. In another example, when the container is in a slanted orientation, some of the air channels may be obstructed by the fluid. Since there can be several other air channels around the sidewall, air exchange is still possible as these other air channels are not obstructed. In yet other embodiments the air channels are constructed sufficiently wide to reduce risk of blockage due to wicking of fluid from capillarity.

Another embodiment features a method of processing a sample, such as preserving or fixing the sample in a fluid. Fixing the sample may suspend the metabolic activities of the cells in the sample.

In one embodiment, the method of preserving a sample in a fluid comprises providing the sample collection container as described herein, providing any valve assembly as described herein to prevent backflow of the fluid from the sample collection container, placing the sample inside the sample collection container, capping the sample collection container with the valve assembly, providing any cap as described herein, attaching the cap to the valve assembly, and releasing the fluid into the container to contact the sample in the sample collection container.

In another aspect, a method is disclosed for processing a sample. The method may comprise providing any sample collection container as described herein, providing any valve assembly as described herein to prevent backflow of the fluid from the sample collection container, placing a sample inside the sample collection container, capping the sample collection container with the valve assembly, providing any cap as described herein, attaching the cap to the valve assembly, releasing the fluid into the container, contacting the fluid with the sample contained in the sample collection container, placing the sample collection container in a holding well of a carrier assembly, placing the carrier assembly in a transport assembly, and transporting the transport assembly from a first location to a second location.

In some embodiments, an average temperature of the fluid is between about 0° C. and 5° C. For example, the average temperature of the fluid is at most about 5° C. In another embodiment, the average temperature of the fluid is at most about 0° C.

In some embodiments, the carrier assembly further comprises at least one data logging device. In some embodiments, the method may further comprise detecting and storing time and temperature information associated with the sample in the data logger device of the carrier assembly. In other embodiments, the step of detecting the time and temperature information may comprise measuring a temperature of the fluid or the sample, measuring a contact period of time in which the fluid contacts the sample, and storing the temperature and contact period of time measurements. In some embodiments, the time and temperature information associated with the sample is detected while the transport assembly is transported from the first location and the second location.

In some embodiments, the sample collection container is capped with the valve assembly such that the valve is disposed inside the sample collection container. In other embodiments, the cap is attached to the valve assembly such that the valve actuator flexure is positioned between the base and the cap.

In some embodiments, the fluid is released into the container by depressing the plunger to break the primary seal and push upon the support top surface of the support structure to compress the spring. The arm then passes through the arm aperture (134) and pushes upon the valve top surface. The valve flexes such that the valve top surface is pushed away from the base bottom surface to allow for the fluid to flow out of the broken seal, through the drain apertures, and into the sample collection container.

In some embodiments, the step of providing the sample comprises inserting a sampling device in a body cavity, collecting the sample from the body cavity with the sampling device, and removing the sampling device from the body cavity. The sample can be collected by a sample collecting portion of the sampling device. For example, the sample collecting portion may be an absorbent swab, a needle, or a biopsy punch tool.

In some embodiments, the step of placing the sample inside the sample collection container comprises inserting the sample collecting portion that has the sample into the container and separating the sample collecting portion from the sampling device such that the sample collecting portion and the sample are disposed inside the container. In other embodiments, the sample can be placed inside the container by inserting the sample collecting portion that has the sample into the container and extracting the sample from the sample collecting portion such that only the sample is disposed inside the container.

In some embodiments, the primary seal may be constructed from a non-reactive and flexible material. Preferably, the primary seal is sufficiently thin to allow for the seal to be broken by the plunger.

In some embodiments, the first end of the spring is attached to the base of the valve housing. For example, the first end of the spring may be attached anywhere on the base. The first end may be attached near or at the periphery of the base. Alternatively, the first end may be attached near or at the center of the base. In some embodiments, the second end of the spring is attached to the support structure. For example, the second end of the spring may be attached anywhere on the support structure. The second end may be attached near or at the periphery of the support structure. Alternatively, the second end may be attached near or at the center of the support structure. In some embodiments, the support structure may comprise a plurality of springs, such as about 2, 3, 4, or 5 springs.

In some embodiments, the arm may be disposed on the support bottom surface. In some embodiments, the arm projects outwardly and away from the support structure. Alternatively, the support structure may comprise a plurality of arms, such as about 2, 3, 4, or 5 arms.

In some embodiments, the drain aperture, and the arm aperture (134) are disposed on the base. In some embodiments, the valve housing may comprise a plurality of drain apertures, such as about 2, 3, 4, or 5 drain apertures. In some embodiments, the valve housing may comprise a plurality of arm apertures, such as about 2, 3, 4, or 5 arm apertures.

In some embodiments, the valve can also be "flexed" with the plunger or actuator, or the valve can be translated. If the valve is translated, the valve does not need to flex, which would possibly allow for more material choices for the valve.

Any feature or combination of features described herein are included within the scope of the disclosure provided that the features included in any such combination are not mutually inconsistent as will be apparent from the context, this specification, and the knowledge of one of ordinary skill in the art. Additional advantages and aspects will become apparent from the following detailed description and claims.

BRIEF DESCRIPTION OF THE DRAWINGS

FIG. 1A-FIG. 1F illustrate conventional sample transport assemblies in various configuration. FIG. 1A is an assembly with an intact internal seal. FIG. 1B illustrates the same container after the seal has been punctured. FIG. 1C illustrates the container in an upright configuration after all fluid has drained from the cap to the container. FIG. 1D illustrates the container from FIG. 1C immediately after inversion. FIG. 1E illustrates the container from FIG. 1C in an inverted configuration after all fluid has drained from the container to the cap. FIG. 1F illustrates the container from 1C when stored in a horizontal configuration.

FIG. 2A-FIG. 2E are schematics illustrating sample transport assemblies of various configuration. FIG. 2A is an assembly in a closed configuration immediately after adding the sample and assembling the container. FIG. 2B illustrates the same container immediately after the valve has been switched to the open configuration. FIG. 2C illustrates the container in an upright configuration after all fluid has drained from the cap to the container and the valve has returned to the closed configuration. FIG. 2D illustrates the container from FIG. 2C when stored inverted. FIG. 2E illustrates the container from FIG. 2C when stored in a horizontal configuration.

FIG. 3A-3C illustrate exemplary valve assemblies incorporating material having inherent resiliency. FIG. 3A is the valve in the closed configuration. FIG. 3B is the valve of 3A in the open configuration, wherein the material having inherent resiliency deforms at an outer periphery. FIG. 3C is the valve of FIG. 3A in the open configuration, wherein the material having inherent resiliency forms part of the valve stem, which stretches in the open configuration.

FIG. 4A-FIG. 4B illustrate another exemplary valve assemblies incorporating material having inherent resiliency. FIG. 4A is the valve in the closed configuration. FIG. 4B is the valve of FIG. 4A in the open configuration, wherein the material having inherent resiliency deforms at an outer periphery.

FIG. 5A-FIG. 5D show an exemplary valve assembly, wherein a seal of the valve is contacted with a resilient mechanism to effect switching the valve from the open to the closed configuration. FIGS. 5A and 5C illustrate valves in the closed configuration. FIGS. 5B and 5D illustrate valves in the open configuration. FIGS. 5A and 5B involve resilient mechanisms that compress when in the open configuration. FIGS. 5C and 5D involve resilient mechanisms that stretch when in the open configuration.

FIG. 6A-FIG. 6D show another exemplary valve assembly, wherein a seal of the valve is contacted with a resilient mechanism to effect switching the valve from the open to the closed configuration. FIGS. 6A and 6C illustrate valves in the closed configuration. FIGS. 6B and 6D illustrate valves in the open configuration. FIGS. 6A and 6B involve resilient mechanisms that compress when in the open configuration. FIGS. 6C and 6D involve resilient mechanisms that stretch when in the open configuration.

FIG. 7A-FIG. 7D show another exemplary valve assembly, wherein a seal of the valve is contacted with a resilient mechanism to effect switching the valve from the open to the closed configuration. FIGS. 7A and 7C illustrate valves in the closed configuration. FIGS. 7B and 7D illustrate valves in the open configuration. FIGS. 7A and 7B involve resilient mechanisms that stretch when in the open configuration. FIGS. 7C and 7D involve resilient mechanisms that compress when in the open configuration.

FIG. 8A-FIG. 8I show another exemplary valve assembly, wherein a seal of the valve is contacted with a resilient mechanism that rotates to effect switching the valve from the open to the closed configuration. FIGS. 8A, 8D, and 8G illustrate valves in the closed configuration. FIGS. 8B, 8E, and 8H illustrate valves switching into the open configuration. FIGS. 8C, 8F, and 8I illustrate valves switching from the open configuration to the closed configuration. FIGS. 8A-8F illustrate configurations in which the seal contacts an internal wall to create a barrier against fluid flow in the closed configuration. FIGS. 8G-8I illustrate configurations in which the seal is pressed against a surface containing apertures to create a barrier against fluid flow in the closed configuration.

FIG. 9A-FIG. 9C show another exemplary valve assembly, wherein a seal of the valve is contacted with a resilient mechanism that bends to effect switching the valve from the open to the closed configuration. FIG. 9A illustrates the valve in the closed configuration. FIG. 9B illustrates the valve switching into the open configuration. FIG. 9C illustrates the valve switching from the open configuration to the closed configuration.

FIG. 10A-FIG. 10D illustrate an embodiment of a flapper valve assembly. FIG. 10A illustrates the flapper valve in the closed configuration. FIG. 10B illustrates the flapper valve in the open configuration. FIG. 10C illustrates the flapper valve switching from the open configuration to the closed configuration. FIG. 10D illustrates the flapper valve in an inverted position, illustrating how the retaining mechanism holds the valve in the closed configuration against the weight of the fluid.

FIG. 17A shows a cross-sectional view of FIG. 14. FIG. 17B shows a cross-sectional view of FIG. 15.

FIG. 23 shows an embodiment of the disclosed assembly.

DETAILED DESCRIPTION

Figure 7A:
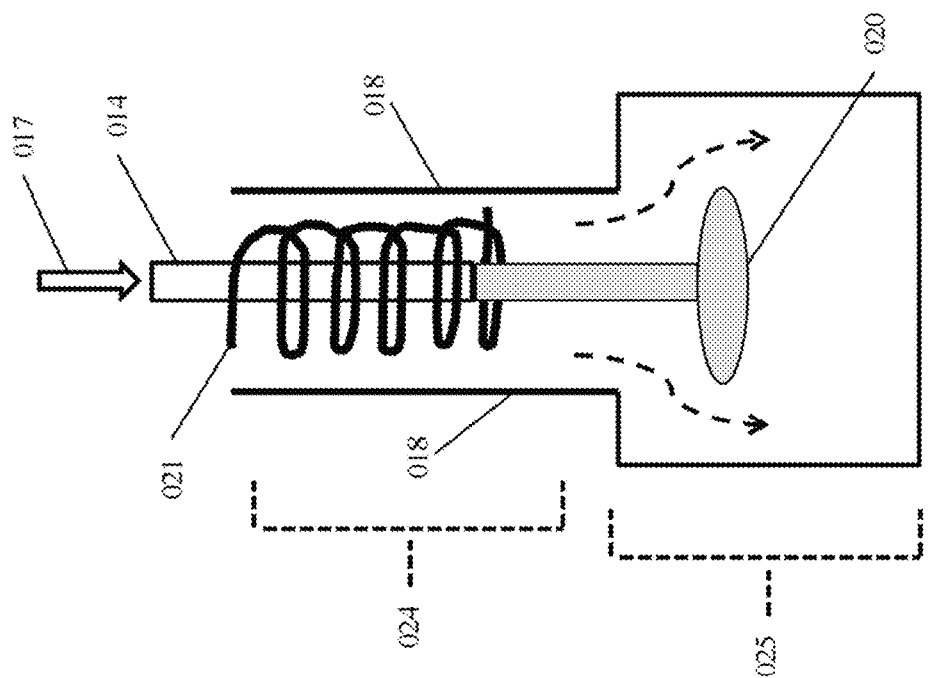

Many medical diagnostics tests require the use of fixed tissue samples, which necessitates the use of large volumes of tissue fixative solutions. Many commonly used tissue fixative solutions are suspected of being hazardous. For example, formalin is suspected of being carcinogenic. Therefore, it is important to minimize the exposure of laboratory technicians to the fixative solutions being used.

One strategy for minimizing fixative exposure is to provide a sample storage and transport container containing a volume of fixative solution sequestered in a portion of the container. Such an arrangement is illustrated at FIG. 1. The container essentially comprises a lower chamber (001) for holding the tissue sample and an upper chamber (002) pre-filled with a fixative solution (003). A frangible seal (004) is disposed in the upper chamber (002) to sequester the fixative solution (003) in the upper chamber (002) until it is ready to dispense into the lower chamber (001). Once a tissue sample (005) is deposited in the lower chamber (002), the user attaches the upper chamber (002) to the lower chamber (001) (FIG. 1A). Once the chambers are attached, a mechanism is activated that introduces a tear (006) in the frangible seal (004), and the fixative solution (003) flows through the tear (006) and into the lower chamber (001) (FIG. 1B). The tissue sample (005) is completely immersed in the fixative solution (004) in the lower chamber (001) as long as the upper chamber is positioned above the lower chamber (FIG. 1C). If, however, the container is inverted (FIGS. 1D & 1E) or placed on its side (FIG. 1F), the fixative solution is free to flow (008) through the tear (006) and back into the upper chamber (002), which can result in a sample that is either completely (005a) or partially (005b) outside of the fixative solution and exposed to air for a substantial period of time. This compromises the integrity of the tissue sample. Moreover, it is not always obvious whether the container has been placed in a position that would cause such backflow of fixative solution.

The disclosed system addresses this problem by placing a valve between the upper and lower chamber. The valve is openable to permit fluid flow from the upper to the lower chamber, and automatically closes to prevent backflow of the fluid from the lower chamber to upper chamber when the container is inverted or placed on its side. The general concept is illustrated at FIG. 2. A tissue sample (005) is deposited in the lower chamber (001) and the upper chamber (002) is attached to the lower chamber (001). When attached, the valve (009) is in a closed configuration (009a), which prevents flow of the fixative solution (003) from the upper chamber (002) to the lower chamber (001) (FIG. 2A). An operator activates an actuator (not shown), which causes the valve enter an open configuration (009b) that creates a multitude of channels (010) through which fixative solution (003) can flow from the upper chamber to the lower chamber (011) (FIG. 2B) and air can be vented from the lower chamber (001) to the upper chamber (002) in exchange. When the operator deactivates the actuator, the valve automatically returns to the closed configuration (009a), thereby sequestering the fixative solution (003) in the lower chamber (001) with the tissue sample (005) immersed therein. The tissue sample (005) remains immersed in fixative solution (003), even when the container is inverted (FIG. 2D) or placed on its side (FIG. 2E).

I. Valve Assemblies

Valve assemblies are provided for selectively permitting flow of fluid. The valve assemblies generally comprise: (1) a valve moveable between an open configuration and closed configuration; and (2) an actuator adapted to apply a first force to the valve, which switches the valve from the closed configuration to the open configuration.

A. Valves

The first force applied to the valve switches the valve from the closed to the open configuration. The valve is generally configured such that, in the absence of the first force, the valve automatically reverts back to the closed configuration.

In one valve arrangement, the valve includes a material having an inherent resiliency that forms at least part of the barrier between the first and second chambers. As used herein, a "material having inherent resiliency" is any material that has a tendency to deform when a force is applied to its surface, but has a tendency to return to its original shape when the force is removed. The first force causes the material to deform, which creates a channel between the first and second chambers through which fluid can flow. When the first force is removed, the inherent resiliency of the material causes the material to return to its original shape, which closes the channel, thereby preventing backflow of fluid from the second chamber to the first chamber regardless of how the assembly is oriented. The actuator in this embodiment may include rigid members that can be placed in contact with a surface of the material to cause deformation. Thus, for example, application of the second force to the actuator moves the rigid members into contact with the material having inherent resiliency and causing the material to deform, thereby putting the valve in the open configuration. The movement of the rigid members toward the material may also generate a third force that acts upon the actuator counteracting the second force, such that when the second force is removed, the third force causes the rigid members to move away from the material. For example, a resilient mechanism placed in contact with the actuator is bent, compressed, stretched, twisted, or rotated when the actuator is moved toward the material, which introduces tension into the resilient mechanism. The tension built into the resilient mechanism exerts the third force on the actuator so that, when the second force is removed, the actuator is forced away from the material and the material is allowed to return to its original shape. Additionally or alternatively, the third force may be exerted on the actuator by the material having inherent resiliency. Deforming the material introduces tension into the system, the tension tending to return the material to its original shape. Thus, when the second force is applied to the actuator and the rigid members deform the material, a third force is applied on the actuator by the tension accumulating in the material. As long as the second force is maintained, the tension will be retained in the material. When the second force is removed, however, the tension is released, causing the material to return to its original shape and forcing the actuator away from the material. Examples of valves incorporating such material having inherent resiliency include, for example, umbrella valves and duckbill valves. Non-limiting illustrations of valves incorporating material having inherent resiliency are displayed at FIGS. 3 and 4.

In FIG. 3, a valve (009) is secured against a surface (012) situated between the first chamber and the second chamber. The surface (012) has a first aperture (013) for permitting a portion of the actuator (014) to contact the valve, and one or more second apertures (015) for permitting fluid flow past the surface. The valve is constructed of a resilient material having a top surface (illustrated by vertical hatch marks) and a bottom surface (illustrated by diagonal hatch marks), and is fixed to the surface (012) via a valve stem (016). As illustrated in FIG. 3A, the valve stem (016) holds the top surface of the resilient materials tightly against the surface (012) so as to seal the second aperture(s) (015) and prevent fluid flow past the surface (012). As illustrated in FIG. 3B, when the second force (017) is applied to the actuator (014), the actuator (014) moves through the first aperture (013) and contacts the top surface of the resilient material, causing the resilient material to deform and cause the top surface of the resilient material to deform away from the surface (012) around the valve stem (016), which opens the second aperture(s), thereby permitting fluid flow (illustrated by the hatched arrow). Deformation causes tension to build in the resilient material, such that when the second force (017) is removed and the actuator (014) moves away from the top surface of the resilient material, the tension is released, causing the top surface of the valve to flex back toward the surface (012) to the configuration in FIG. 3A, thereby resealing the second aperture(s). As illustrated in FIG. 3C, a similar effect could be realized by constructing the valve (009) with a valve stem (016) made of the material having an inherent resiliency or includes a resilient mechanism. In such an arrangement, the valve stem (016) would deform by stretching, causing the top surface to move away from the surface (012) and introducing tension into the valve stem (016). When the second force (017) is removed and the actuator (014) moves away from the top surface of the resilient material, the tension is released, causing the valve stem (016) to pull the top surface back to the configuration in FIG. 3A, with the top surface of the valve in contact with the surface (012) and resealing the second aperture(s) (015).

In FIG. 4, a valve (009) is disposed at a point between the first chamber and the second chamber and secured in place by a valve stem (016). In the closed configuration as illustrated in FIG. 4A, the valve (009) is disposed such that an outer periphery of the valve (009) fits snugly against an interior wall (018) that defines a channel through which fluid can flow from the first chamber to the second chamber. The valve (009) in this configuration thus provides a barrier that prevents fluid exchange between the first and second chambers. As illustrated in FIG. 4B, when the second force (017) is applied to the actuator (014), the actuator (014) contacts the resilient material, causing the periphery of the resilient material to deform away (019) from the inner wall (018), which creates a gaps through which fluid flow can occur (illustrated by the hatched arrow). Deformation causes a force to build in the resilient material, such that when the second force (017) is removed and the actuator (014) moves away from the resilient material, the force of the resilient material causes the outer periphery of the valve (009) to flex back toward the inner wall (018) to resume the closed configuration in FIG. 4A, thereby resealing the channel.

In another embodiment, the valve comprises: (1) a seal; and (2) a resilient mechanism connected to the seal. In the closed configuration, the resilient mechanism holds the seal in a position that creates a barrier to fluid flow. The first force moves the seal to create a channel through which fluid can flow, and the resilient mechanism creates a force tending to cause the seal to return to closed configuration, for example, by compressing, extending, bending, or twisting the resilient mechanism. When the first force is released, the force generated by the resilient mechanism moves the seal back into the closed configuration. Non-limiting examples of resilient mechanisms include: springs (including extension springs, compression springs, and torsion springs), such as coil springs, flat springs, machined springs, leaf springs, serpentine springs, gas springs, negator springs, cantilevered springs, V-springs, Belleville springs, wave spring, constant force springs, progressive rate coil springs; elastic bands (such as rubber bands and bands of elastic polymers); magnetic mechanisms, and the like. The resilient mechanism must have sufficient resiliency such that it securely holds the seal in a position that prevents fluid exchange between the first and second chambers after the first force is removed.

Additionally, the seal may, when in the open configuration, contain one or more channel(s) through which air can be exchanged between the first and second chambers. The fluid and air channels may be the same or different channels.

Non-limiting illustrations of seal/resilient mechanisms are displayed at FIGS. 5-10.

FIG. 5 illustrates a non-limiting example in which the seal (020) is held against a surface containing second apertures for fluid flow (015). In FIGS. 5A and 5B, the resilient mechanism (021) is designed to be tensioned when compressed. The resilient mechanism (021) is disposed between a bottom surface (022) proximate to the second chamber and the seal (020), and the seal (020) is disposed between the resilient mechanism (021) and a top surface (023) proximate to the first chamber. The top surface (023) contains a first aperture (013) for permitting a portion of the actuator (014) to contact the seal (020), and both the top (023) and bottom (022) surfaces contain second aperture(s) (015) for permitting fluid flow and/or air exchange between the first and second chambers. As illustrated in FIG. 5A, in the closed position the seal (020) is pressed against the top surface (023) by the resilient mechanism (021) so as to prevent fluid flow through the second aperture (015). As illustrated in FIG. 5B, when the second force (017) is applied to the actuator (014), the actuator (014) moves through the first aperture (013) and presses on the seal (020). The resilient mechanism (021) is compressed, and the seal moves away from the top surface (023), thereby allowing fluid to flow between the second apertures (015) (illustrated by the hatched arrow). when the second force is removed, the force of the compressed resilient mechanism (021) pushes the seal back against the top surface (023), thereby preventing fluid exchange through the second aperture (015) of the top surface (023). In FIGS. 5C and 5D, the resilient mechanism (021) is designed to be tensioned when extended. The resilient mechanism (021) is attached to the seal (020) at one end and a top surface proximate to the first chamber (022) at the other end, and the seal (020) is disposed between the top surface (022) and a bottom surface (023) proximate to the first chamber. The top surface (023) contains a first aperture (013) for permitting a portion of the actuator (014) to contact the seal (020), and both the top (023) and bottom (022) surfaces contain second aperture(s) (015) for permitting fluid flow and/or air exchange between the first and second chambers. As illustrated in FIG. 5C, in the closed position the seal (020) is pulled against the top surface (023) by the resilient mechanism (021) so as to prevent fluid flow through the second aperture (015). As illustrated in FIG. 5D, when the second force (017) is applied to the actuator (014), the actuator (014) moves through the first aperture (013) and presses on the seal (020). The resilient mechanism (021) is stretched, and the seal moves away from the top surface (023), thereby allowing fluid to flow between the second apertures (015) (illustrated by the hatched arrow). When the second force is removed, the force of the stretched resilient mechanism (021) pushes the seal back against the top surface (023), thereby preventing fluid exchange through the second aperture (015) of the top surface (023).

Figure 7B:
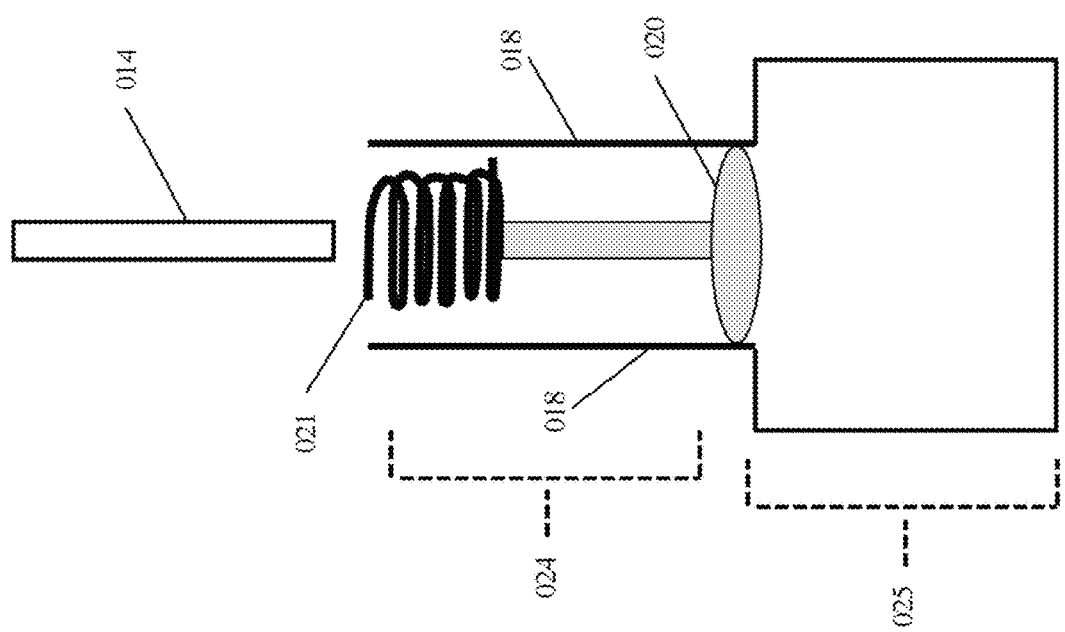

FIGS. 6 and 7 illustrate non-limiting examples in which the seal is disposed between inner walls of a cylinder (018). Application of the second force (017) causes the seal (020) to move from a first position and second position, while the resilient mechanism (021) is positioned to generate a force tending to return the seal (020) from the second position to the first position when compressed (FIGS. 6B and 7B) or stretched (FIGS. 6D and 7D). The cylinder is sized such that, in the first position an outer periphery of the seal (020) snugly fits against the inner walls (018) to create the barrier between the first and second chambers (see FIGS. 6A, 6C, 7A, and 7C), and, in the open position a gap is formed between the inner walls (018) and the seal (020) to define the channel through which fluid can be exchanged between the first and second chambers (illustrated by hatched arrows) (see FIGS. 6B, 6D, 7B, and 7D). For example, the inner walls (018) may define a frustroconical cylinder that is narrower in the first position than second position (see FIG. 6). In another example, the inner walls (018) may define a first cylinder that is fit to second cylinder, the first cylinder being narrower than the second cylinder, such that movement of the seal from the first position to the second position moves the seal from the first cylinder to the second cylinder (see FIG. 7). In this example, the first cylinder may be, for example, an aperture in a valve support, and the second cylinder may be the first or second chamber, such that the second force moves the seal from the first cylinder into the first or second chamber. Alternatively, the valve support may contain both the first and the second chambers. When the second force (017) is applied to the actuator (014), the actuator (014) presses on the seal (020) and the resilient mechanism (021) is compressed (FIGS. 6B and 7B) or stretched (FIGS. 6D and 7D), and the seal moves from the first position to the second position, thereby allowing fluid to flow between the first and second chamber (illustrated by the hatched arrows). When the second force is removed, the force of the stretched or compressed resilient mechanism (021) pushes the seal (020) back to the first position and in contact with the inner wall (018), thereby preventing fluid exchange.

FIG. 8 illustrates non-limiting examples in which the seal is rotated around the resilient mechanism to switch between the open and closed configuration. The resilient mechanism (021) is attached to the seal (020) in an arrangement that allows the seal (020) to rotate around the resilient mechanism (021). Application of the second force (017) on the actuator (014) causes the actuator to press an edge of the seal (020), thereby causing the seal (020) to rotate from the closed to the open position (024) to creates a channel through which fluid can flow (illustrated by the hatched arrows). Rotation of the seal causes torque to accumulate in the resilient mechanism (021) (see FIGS. 8B, 8E, and 8H). When the second force (017) is removed, the torque is released, forcing the seal (020) to rotate back to the closed position (025), thereby preventing fluid flow between the first and second chambers. The resilient mechanism (021) can be arranged such that the seal (020) rotates at an outer edge (see FIGS. 8A-8C and 8G-8I), or around a point toward the center of the seal (020) (see FIGS. 8D-8F). The seal (020) can be positioned to fit snugly against an inner wall (018), such that rotation of the seal (020) to the open position creates a gap between the inner wall (018) and the seal (020), or, the seal (020) can be configured to create a barrier against an inner surface (022) containing second apertures (015) for permitting fluid flow and first apertures (013) permitting contact between the actuator (014) and the seal (020).

FIG. 9 illustrates a non-limiting embodiment in which the resilient mechanism (021) comprises a rigid member that is bent in response to the application of the second force (017) to the actuator (014). The resilient mechanism (021) is arranged such that the rigid members contacted to a surface of the seal (020) in a manner that holds the seal (020) in the closed configuration (see FIG. 9A). Application of the second force (017) to the actuator (014) pushes the seal (020) against the rigid member of the resilient mechanism (021), causing the rigid member to bend (026) and allowing the seal (020) to move to a sufficient degree to create a channel through which fluid can flow past the seal (illustrated by hatched arrows) (see FIG. 9B). Bending (026) may be within the rigid member itself, or the rigid member may be connected to, for example, a torsion spring. In either case, a force is generated as a result of the bending, such that when the second force is removed, the force in the rigid member causes the rigid member to straighten (027), thereby forcing the seal (020) back into the closed position.

Figure 10D:
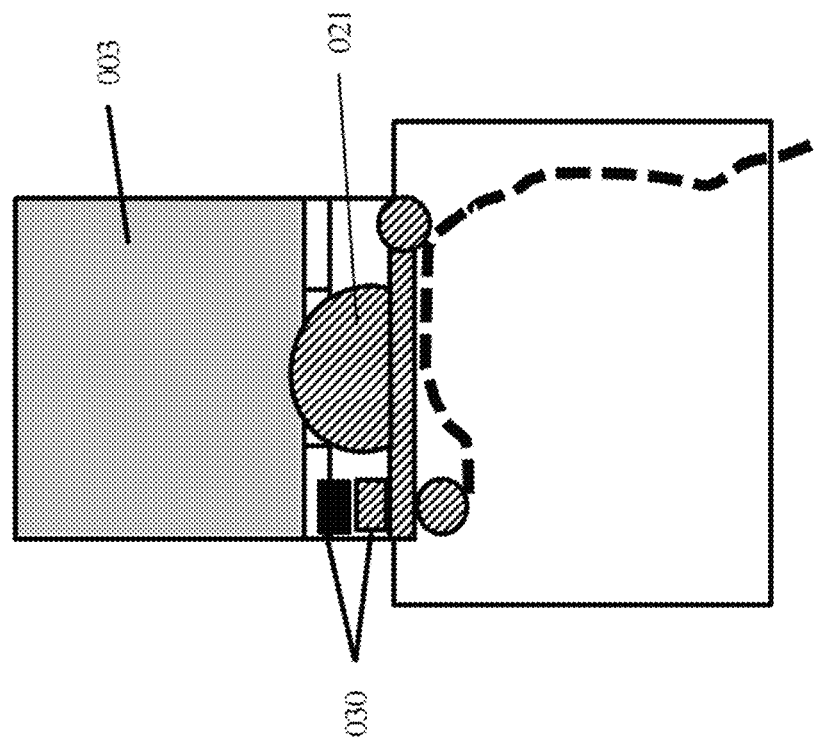
Figure 10C:
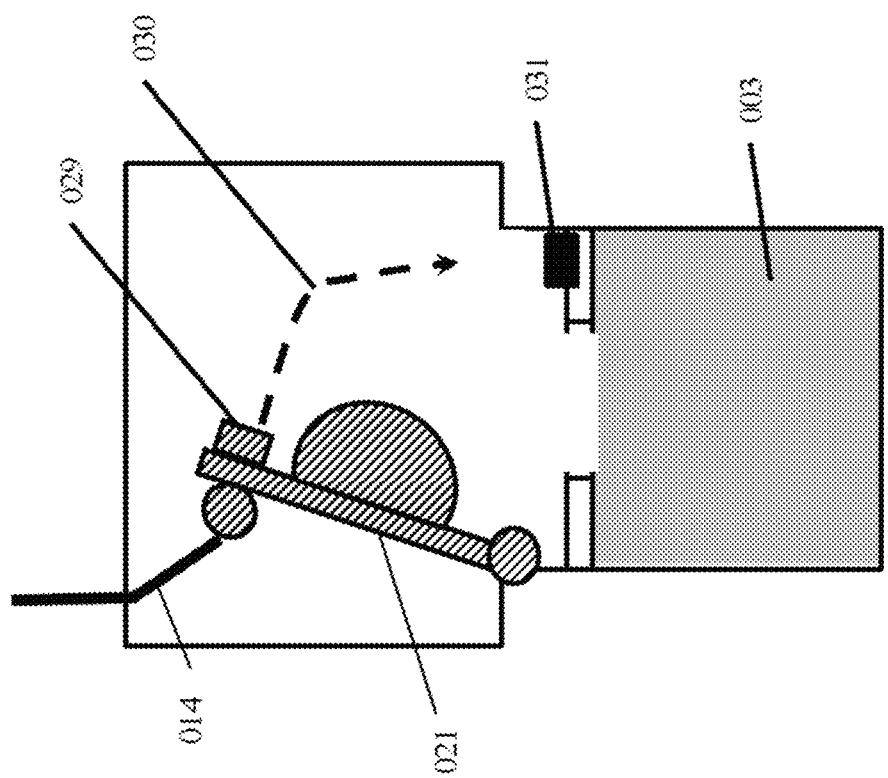

In some configurations, the first force switches the valve from the closed to the open configuration, but is not required to keep the valve in the open configuration. One such example is a flapper valve, a non-limiting embodiment of which is illustrated at FIG. 10. The valve comprises a seal (021) constructed of a material and with a shape such that it is buoyant in the fixative solution. The seal (021) is disposed such that it snugly fits in an aperture (015) connecting the first and second chambers in the closed configuration (see FIG. 10A). The actuator (014) is connected to a first end of the seal (021) and a hinge (028) is disposed at an opposite end of the seal (021), such that application of the second force (017) to the actuator (014) causes the seal (021) to rotate around the hinge (028) and away from the aperture (015). In this position, the inherent buoyancy of the seal holds the seal in the open configuration (029) until sufficient fixative fluid flows through the aperture (illustrated by hatched arrow) (see FIG. 10B). Eventually, insufficient buoyant force remains on the seal (021) to keep it open, and the seal (021) falls back into the closed configuration under its own weight (030) (see FIG. 10C). A holding mechanism, such as paired magnets (031), is disposed along the seal (021) to keep the seal (021) in the closed position until the second force is applied, even when inverted (see FIG. 10D). The holding mechanism must hold the seal (021) firmly enough in place that the force of fluid on the seal (021) will not force the seal (021) open when inverted, but is weak enough that it will not unduly inhibit opening in response to the second force or (in the case of a magnetic mechanism (031)) will not overcome the buoyant force on the seal (021). In such an embodiment, the second force does not need to be maintained on the actuator in order to keep the valve in the open configuration. Rather, the force of the buoyancy is sufficient.

In other examples, the valve is a check valve, and the first force is a fluid pressure exerted on the valve by the actuator, the fluid pressure causing the valve to open. When the fluid pressure falls below a threshold, the valve closes again. Examples of check valves include duckbill valves, ball check valves, swing check valves, and the like.

A ball check valve is a check valve in which the closing member, the movable part to block the flow, is a spherical ball. In an example, a spring-loaded ball check valve is used. The spring is tensioned to hold the ball securely to prevent fluid flow in the absence of increased fluid pressure. The actuator is adapted to increase the fluid pressure in the first chamber, thereby forcing the ball against the spring. When the fluid pressure exceeds the pressure asserted by the spring, the ball moves down and creates a channel through which the fluid flows into the second chamber. When the fluid pressure falls below the force asserted by the spring, the spring forces the ball back into the closed position. The valves illustrated in FIG. 6 could be used in a ball check valve arrangement, except that instead of physical contact between the actuator and seal causing the seal to move to the open position, the fluid exerts the first force on the seal to cause it to move to the open position. Designs are also possible without a spring, if the ball is arranged such that reverse flow or gravity moves the ball toward the seat and create a seal. The interior surface of the main seats of ball check valves are more or less conically-tapered to guide the ball into the seat and form a positive seal when stopping reverse flow.

A swing check valve or tilting disc check valve is check valve in which the disc, the movable part to block the flow, swings on a hinge or trunnion, either onto the seat to block reverse flow or off the seat to allow forward flow. The seat opening cross-section may be perpendicular to the centerline between the two ports or at an angle. An example of this mechanism is the clapper valve, in which a hinged gate only remains open in the inflowing direction. The clapper valve often also has a spring that keeps the gate shut when there is no forward pressure. The valves illustrated in FIG. 8 could be used in a swing check valve arrangement, except that instead of physical contact between the actuator and seal causing the seal to move to the open position, the fluid exerts the first force on the seal to cause it to move to the open position.

A duckbill valve is typically manufactured from an elastomeric material (such as a rubber or synthetic elastomer), with an open end for fitting on a channel for fluid flow and the other end flattened with a slit at the end (much like the beak of a duck). When a fluid is pumped through the valve from the open end to the flat end, the flattened end opens to permit the pressurized fluid to pass. When pressure is removed, however, the duckbill end returns to its flattened shape, preventing backflow. The open end of the valve is typically stretched over a channel connecting the first and second chamber outlet of a supply line with the open end facing toward the first chamber and the flattened end facing toward the second chamber. Thus, pressurize fluid can flow from the first chamber through the valve to the second chamber, but cannot flow in the opposite direction.

In embodiments using a check valve, the actuator is arranged to increase the fluid pressure in the first chamber so as to force the check valve open. One particular arrangement is a plunger similar to those used in syringes. The plunger is friction-fit into the first chamber, such that fluid cannot flow past the plunger. As the plunger is depressed, the fluid is forced toward the valve, increasing the pressure until the valve opens. Pressure is relieved as fluid flows through the valve; therefore, pressure must be maintained on the plunger until sufficient fluid has drained into the second chamber. Once this happens, pressure can simply be released from the plunger, and the valve closes due to fluid pressure falling below the threshold.

In ball check valve arrangements that do not use springs, a primary seal is typically provided in the prefilled cap. The actuator in this case simply needs to release the primary seal (although pressurizing the fluid may also be an effect), allowing fluid to flow into and through the valve. The valve then remains in the open position until it is tipped or inverted, in which case fluid flow and/or the force of gravity carries the ball into the closed position.

B. Actuators

The actuator is typically arranged such that application of the second force to the actuator causes it to apply the first force to the valve, and maintenance of the second force is required to hold the valve in the open position, such that removal of the second force automatically results in the valve reverting to the closed position. One way in which this is accomplished is by placing the actuator in contact with a resilient mechanism configured to counteract the second force. Non-limiting examples of resilient mechanisms include: springs (including extension springs, compression springs, and torsion springs), such as coil springs, flat springs, machined springs, leaf springs, serpentine springs, gas springs, negator springs, cantilevered springs, V-springs, Belleville springs, wave spring, constant force springs, progressive rate coil springs; elastic bands (such as rubber bands and bands of elastic polymers); magnetic mechanisms, and the like. The resilient mechanism is position such that when the actuator moves to apply the first force to the valve, it also causes the resilient mechanism to move, twist, bend, compress, or stretch, which generates a restoring force in the resilient mechanism. The restoring force is generally asserted opposite the second force applied to the actuator, such that as long as the second force remains applied to the actuator, the actuator will continue to hold the valve in the open position. When the second force is removed, however, the restoring force causes the actuator to release the first force on the valve (such as by moving away from the valve) Additionally, the actuator is mechanically connected to a mechanism outside of the container that permits user-initiated application of the second force to the actuator without requiring exposure of the user to the contents of the assembled container. In one simple embodiment, a button is disposed on the container arranged such that when the user depresses the button, the second force is applied to the actuator.

II. Caps and Sample Collection Containers

The valve assemblies described above are especially adapted for use in a sample transport system comprising a cap prefilled with a fixative solution and a sample transport container.

The prefilled cap typically contains a primary seal for holding the fixative solution in the cap until it is ready to be dispensed into the lower chamber. In some cases, the valve assembly may function as the primary seal. In other cases, a separate primary seal may be provided, which functions to sequester the fixative solution from the valve until it is ready to be dispensed.

Any container suitable for holding a biological sample for analysis—especially tissue samples—can be used as the sample transport container. In some embodiments, the second chamber further comprises an apparatus for holding the biological sample, such as a tissue cassette.

The cap and the container are further adapted to fit together with the valve assembly separating their respective chambers. The fit between the various components should be sufficiently snug that no fluid can either leak between the components or out of the assembled container unless the valve is in the open configuration. Preferably, the assembly is fume-safe, i.e. does not emit fixative fluid fumes when completely assembled. Any arrangement in which the three components can fit together can be used. In one example, the valve assembly contains threads that fit with threads on each of the cap and the container. In this arrangement, the cap and container do not need to directly contact one another, as the threads on the valve assembly fix the entire assembly together. In other embodiments, either the cap or the container contains threads for accepting both the valve assembly and the other component. For example, the cap could be provided with internal threads that fit the valve assembly and external threads that accept the container. Alternatively, the container could contain internal threads for accepting the valve assembly and external threads for accepting the cap. In another arrangement, the cap and the container could each fit to one another via threaded fit and could also contain internal ridges for fixing the valve assembly in place. Many other arrangements will be immediately apparent to the person of ordinary skill in the art.

Either the cap or the container further contains a user interaction device that allows the user to activate the actuator without contacting the contents of the assembled container. For example, a button or level may be contacted with a substantially rigid member inside the cap or container such that, when the button or lever is activated, the rigid member applies the second force to the actuator. Alternatively, the actuator may extend outside of the cap or the container, such that the user may directly apply the second force to the actuator. In an example, the cap and the actuator interact like a syringe plunger, with the actuator disposed in a liquid impermeable friction fit in the cap. Many other arrangements will be immediately apparent to the person of ordinary skill in the art.

III. Specific Examples

Figure 11:
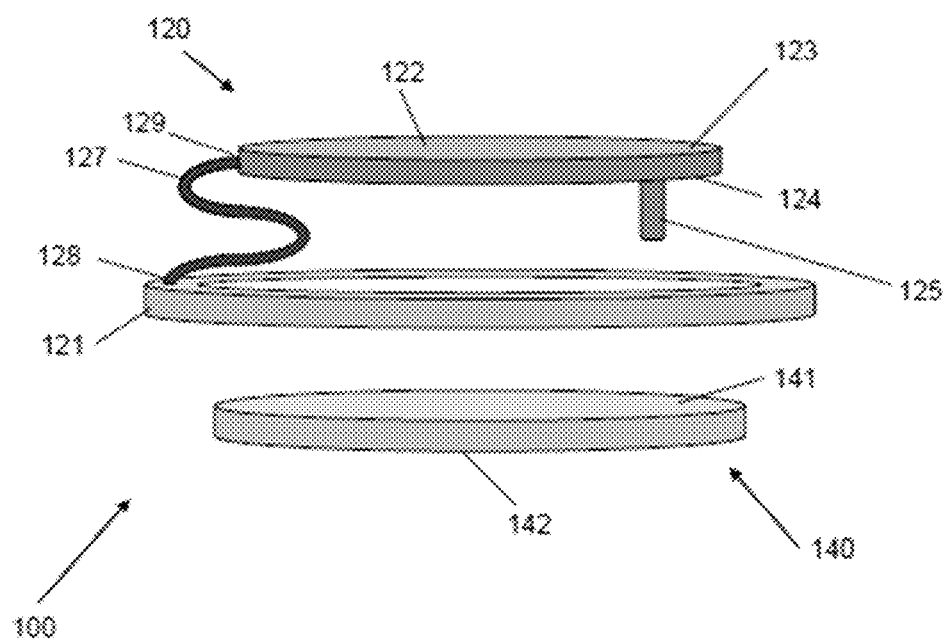
FIG. 11 shows an exploded view of a specific embodiment.

Referring now to FIG. 11-21, a specific embodiment is described. Following is a list of elements corresponding to a particular element referred to herein:
100 valve assembly
101 sample
105 fluid
110 sample collection container
120 valve actuator flexure
121 outer frame
122 support structure
123 support top surface
124 support bottom surface
125 plurality of arms
126 anchor
127 plurality of springs
128 first end
129 second end
130 valve housing
131 base
132 sidewall
133 plurality of drain apertures
134 plurality of arm apertures
135 stem opening
136 base bottom surface
137 channel
140 valve
141 valve top surface
142 valve bottom surface
143 valve stem
144 bulbous stem end
200 plunger
301 frame locking tab
302 housing locking tab
400 air channel
500 Prefilled cap
505 seal This non-limiting embodiment features a sample collection system for preserving a sample (101) in a fluid (105). FIG. 11 illustrates the basic elements of the valve assembly. The valve assembly (100) comprises a valve actuator flexure (120) and a valve (140). The valve actuator flexure (120) comprises an outer frame (121), a support structure (122), and at least one spring (127). The support structure (122) may comprise a support top surface (123), a support bottom surface (124), and at least one arm (125). The arm (125) can be disposed on the support bottom surface (124) and projecting outwardly and away from the support structure (122). In some embodiments, the spring (127) comprises a first end (128) and a second end (129). The first end (128) of the spring (127) can be attached to the outer frame (121) and the second end (129) of the spring (127) can be attached to the support structure (122).

Figure 12:
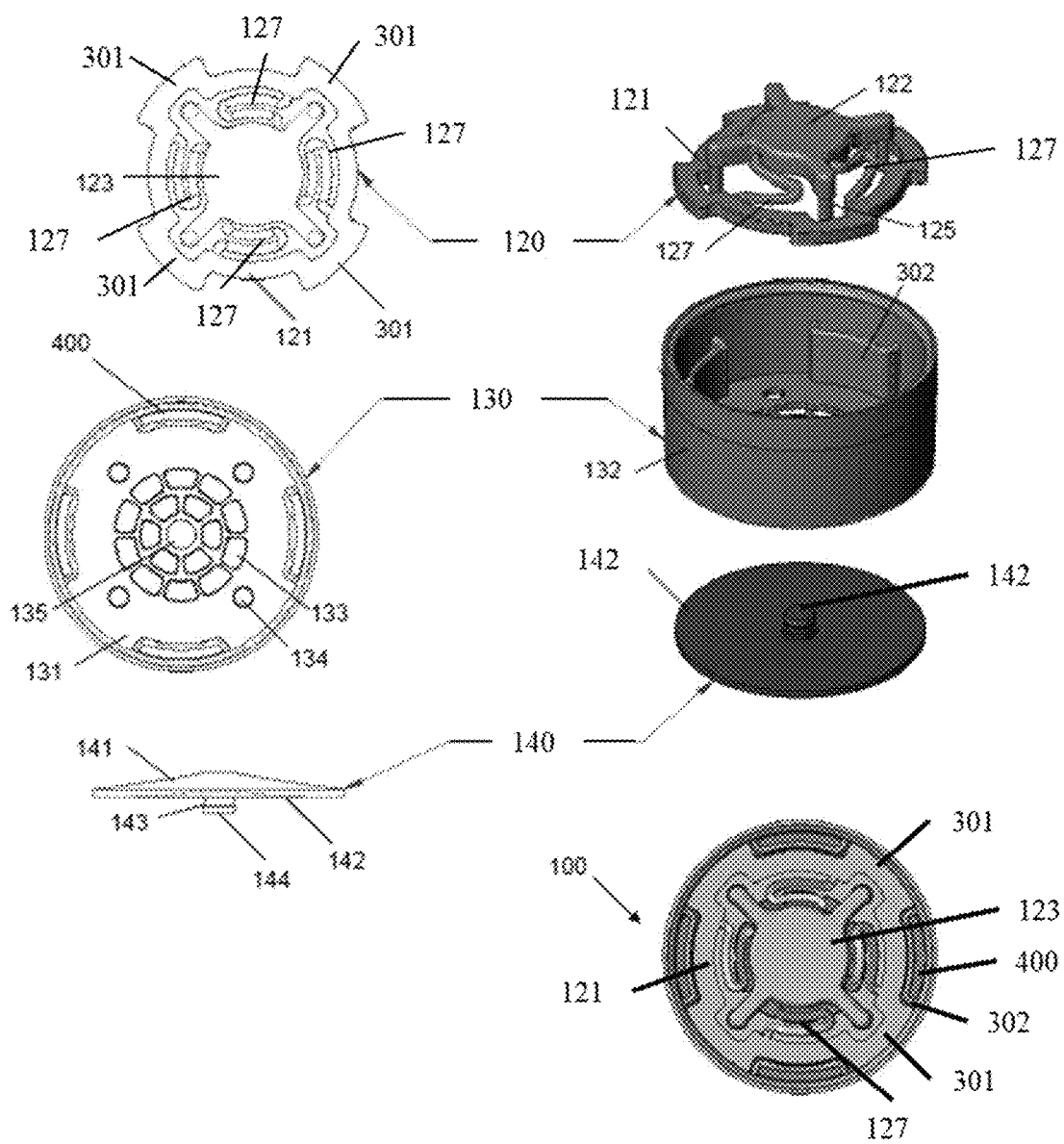
FIG. 12 shows an exploded view of a specific embodiment.
Figure 13A:
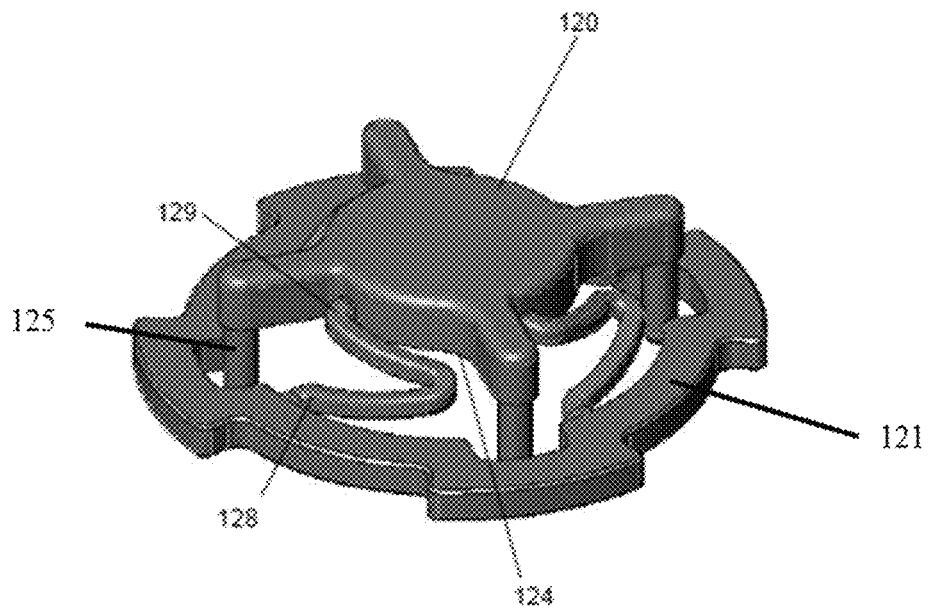
FIG. 13A show a valve flexure of a particular embodiment in an uncompressed position.
Figure 13B:
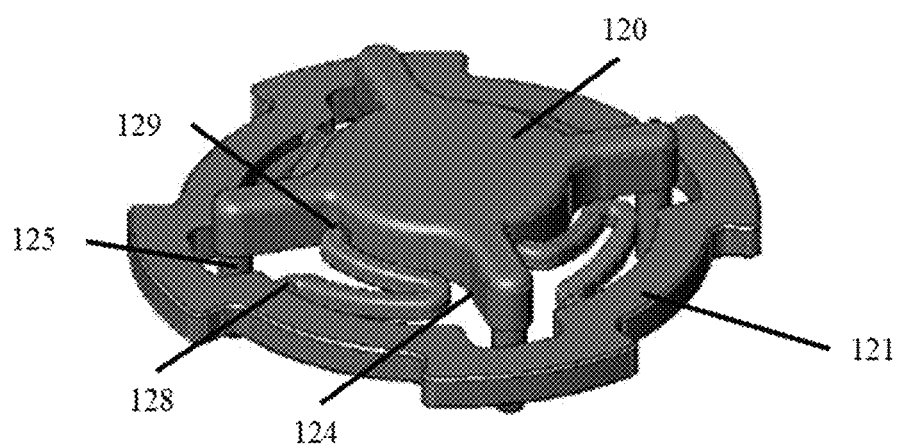
FIG. 13B show the valve flexure in a compressed position.
Figure 14:
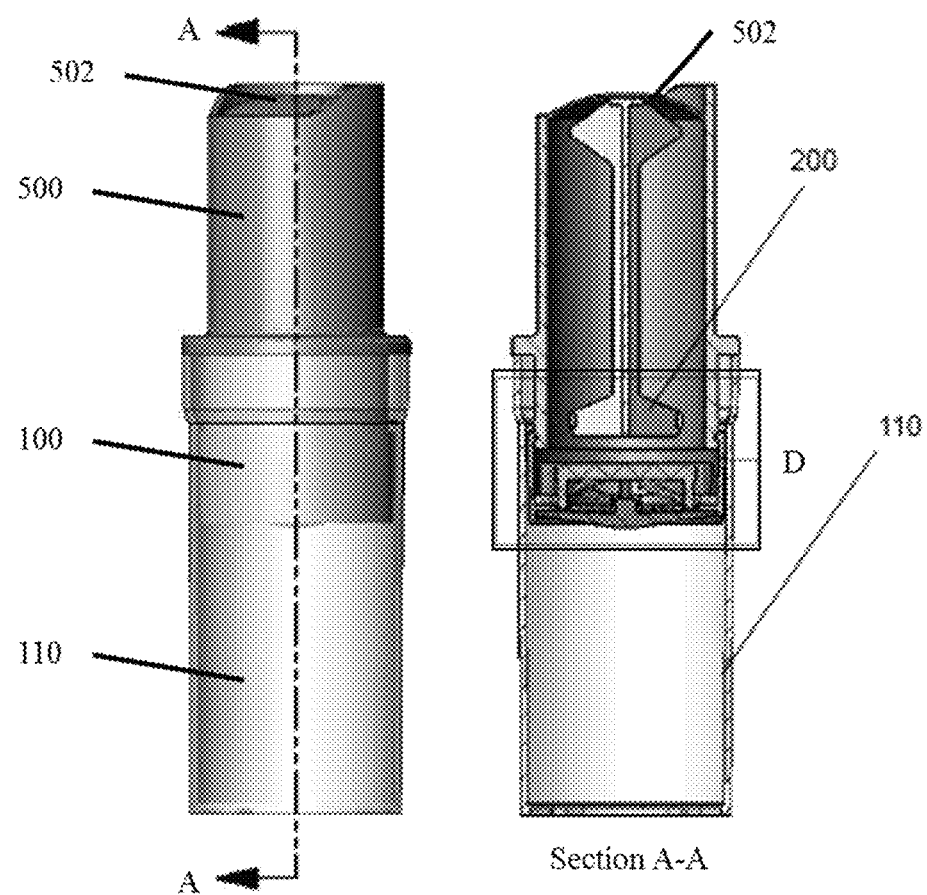
FIG. 14 shows a disclosed assembly in an uncompressed position.

FIG. 12 provides a detailed view of the components of the valve assembly. A valve housing (130) is provided, comprising a base (131), a sidewall (132), at least one drain aperture (133), at least one arm aperture (134), and a stem opening (135). The drain aperture (133), the arm aperture (134), and the stem opening (135) may be disposed on the base (131). The valve (140) comprises a valve top surface (142) and a valve bottom surface (141) and a valve stem (144). The valve stem (144) inserts into the stem opening (135) to hold the valve (140) in position on the bottom side of the base (131) with the top surface (142) held against the bottom surface of the base (131). The valve (140) is disposed beneath the valve actuator flexure (120) such that the valve top surface (141) is in contact with the base bottom surface (136), and the valve actuator flexure (120) is disposed in the valve housing (130) with the support top surface (123) facing away from the valve (140) and the four arms (125) projecting toward the valve top surface (141) and over or through the arm apertures (134). The frame locking tabs (301) fit between the housing locking tabs (302) to prevent the valve actuator flexure (120) from moving (i.e. rotating) in the valve housing (130). The valve (140) is constructed of material with inherent resilience, such that when a force is applied to an outer edge of the valve (140), the valve will bend, but will return to its original shape when the force is removed. As illustrated in FIG. 13, the valve actuator flexure can move from an uncompressed (top image) to a compressed (bottom image) configuration.

In operation, the second force is applied to the support structure top surface (123), which forces the support structure (122) downward. The arms (125) move through the arm apertures (134), placing the arms (125) in contact with, and applying the first force to, a top surface of the valve (140). The first force causes the valve (140) to flex away from the bottom surface of the base (131), creating a channel (137) between the base (131) and the valve (140), thereby permitting fluid to flow through the one or more drain aperture(s) (133). Movement of the support structure (122) also causes the spring(s) (127) to compress. Releasing the second force causes the spring(s) (128) to at least partially relax, which forces the arms (125) to move away from the valve (140), thereby releasing the first force. The inherent resiliency of the valve (140) causes the valve to return to its original configuration in contact with the bottom edge of the base (131), thereby resealing the drain aperture(s) (133).

Figure 16:
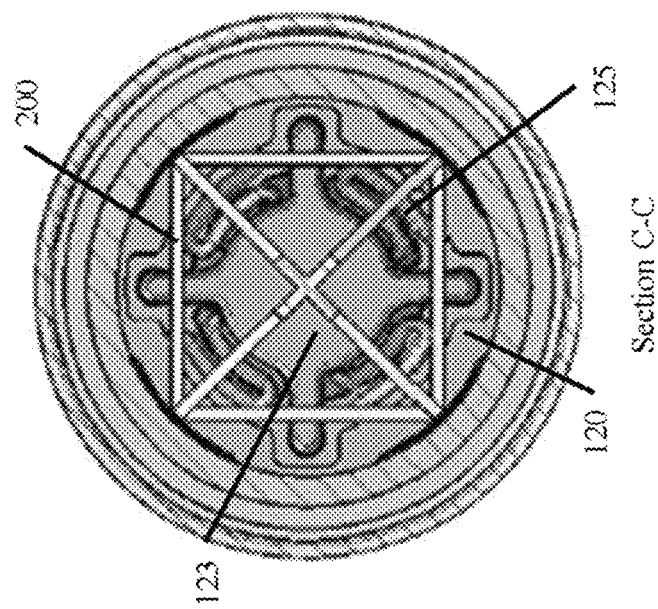
FIG. 16 shows a cross-sectional view of section C-C in FIG. 15.
Figure 15:
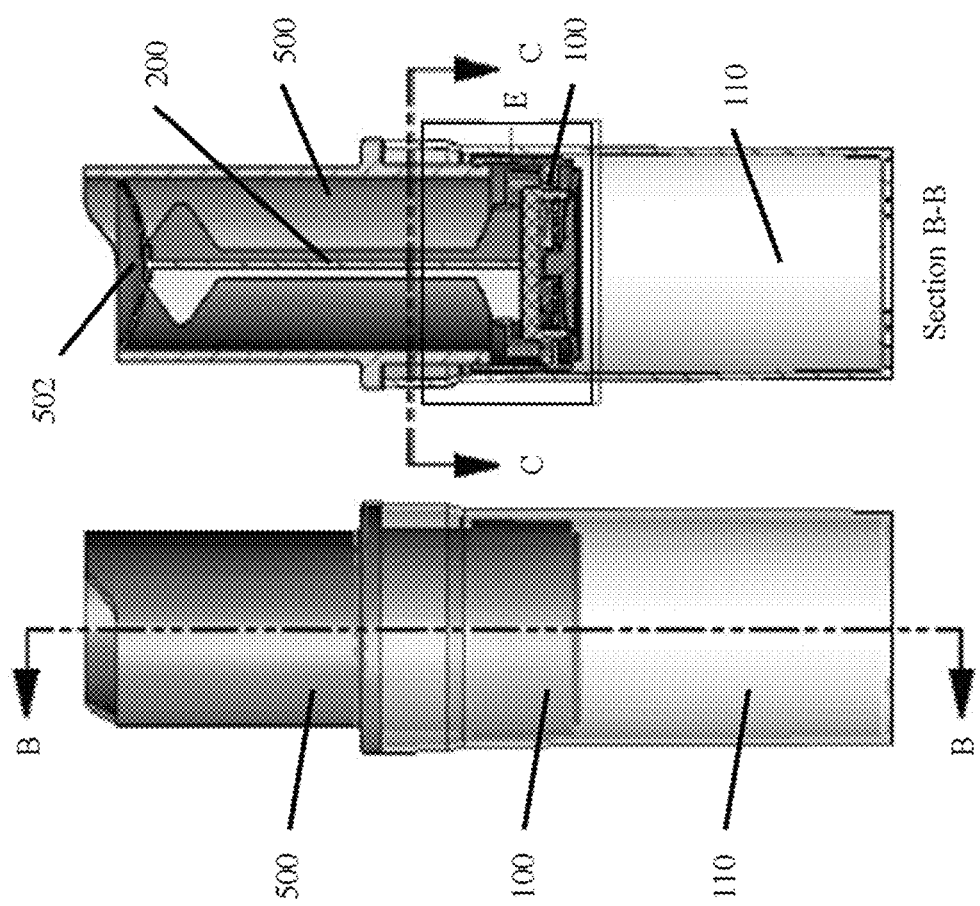
FIG. 15 shows a disclosed assembly in a compressed position.

FIGS. 14-17 are cross-sections of the assembled carrier with the valve in the closed (FIGS. 14 and 17A) and open (FIGS. 15 and 17B) configurations. As can be seen, the valve assembly (100) is disposed between the prefilled cap (500) and the sample collection container (110). The valve may be adapted to be fit into a bottom end of the prefilled cap (500), a top end of the sample collection container (110), or both. Examples of fit include use of threaded fits, retention clips, friction fit, spring ball retainers, or the like. Regardless of the fit used, the valve should be fit into the assembled container such that substantially no gaps exist through which fluid can flow from the cap to the container and vice-versa, except through the valve assembly, regardless of the orientation in which the container is held. The prefilled cap includes a flexible button mechanism (502) at a top side. A plunger mechanism (200) is disposed in the prefilled cap (500), with one end near the flexible button mechanism (502) and a second end near the valve assembly (100), proximate to the support top surface (123). FIG. 16 is a top cross-sectional view showing the arrangement of the plunger (200) and the support top surface (123). As can be seen, the plunger (200) is designed so that it does not substantially inhibit fluid flow, but still provides a substantially rigid interaction with the support top surface (123). As illustrated in FIGS. 15 and 17B, depression of the flexible button mechanism (502), pushes the plunger (200) downward. The arms (125) move through the arm apertures (134) and depress the outer edges of the valve (140), pushing the edges away from the bottom edge of the base (131), which creates a channel (137) through which fluid can flow through the drain apertures (133) and past the valve (140) (see FIG. 17B). When the flexible button mechanism (502) is released, the springs (128) push the support top surface (123) away from the valve (140), and with the arms (125) no longer pressing on the valve top surface (141), the valve (140) flexes back to the closed configuration (see FIGS. 14 and 17A).

In one embodiment, the exemplary valve assembly (100) contains independent air channels (400), which allow for air exchange between the cap and the sample collection. As illustrated at FIGS. 18-21, when the valve initially opens, fluid from the cap displaces air in the sample collection container. This air/liquid exchange can occur through the same apertures in the base as long as the pressure of gravity on the fluid in the cap exceeds the atmospheric pressure. Once the pressure equilibrates, however, fluid exchange will no longer proceed. Thus, it is desirable to provide dedicated air exchange channels (400) throughout the base (131) to ensure complete drainage of fluid from the cap to the sample collection container.

Figures 18A, 18B, 18C:
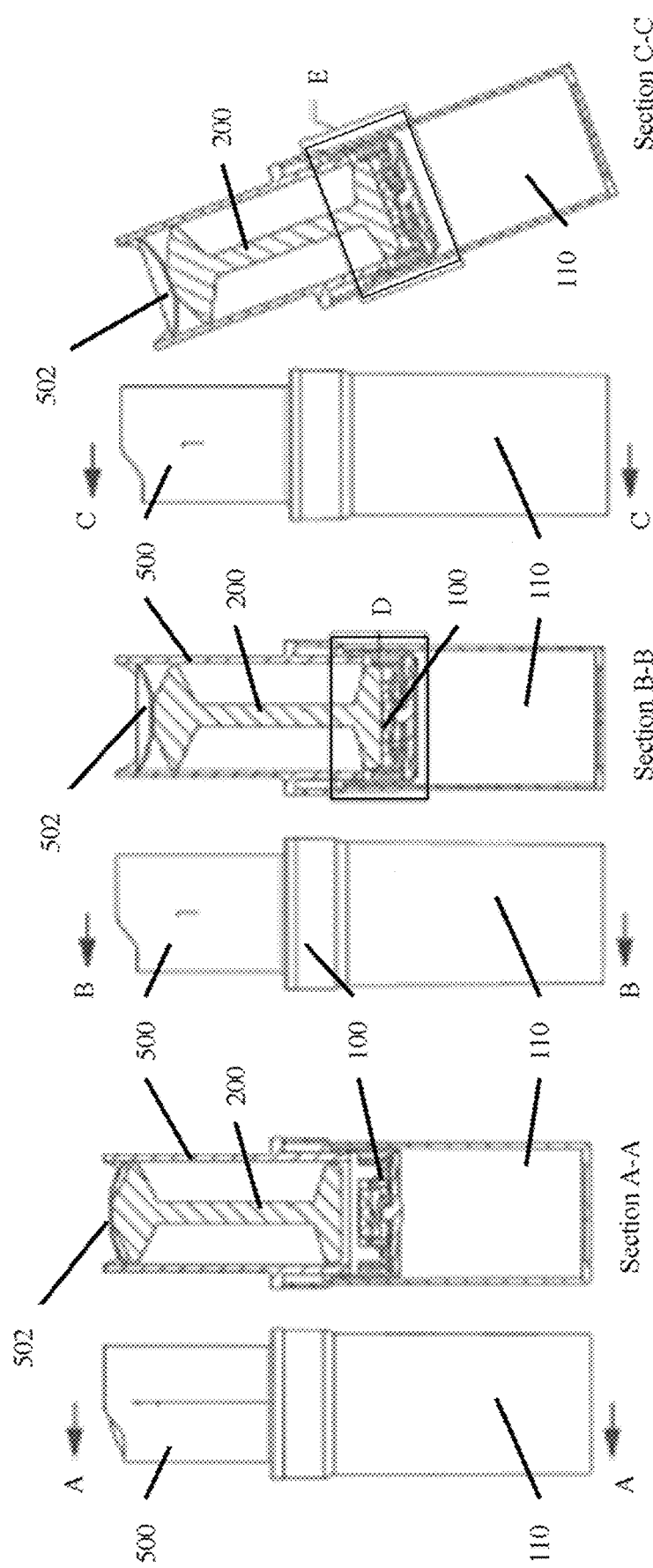
FIG. 18A shows an embodiment of the disclosed assembly in an uncompressed position.
FIG. 18B shows the embodiment of the disclosed assembly in a compressed position.
FIG. 18C shows the embodiment of the disclosed assembly in a slanted orientation.
Figure 19B:
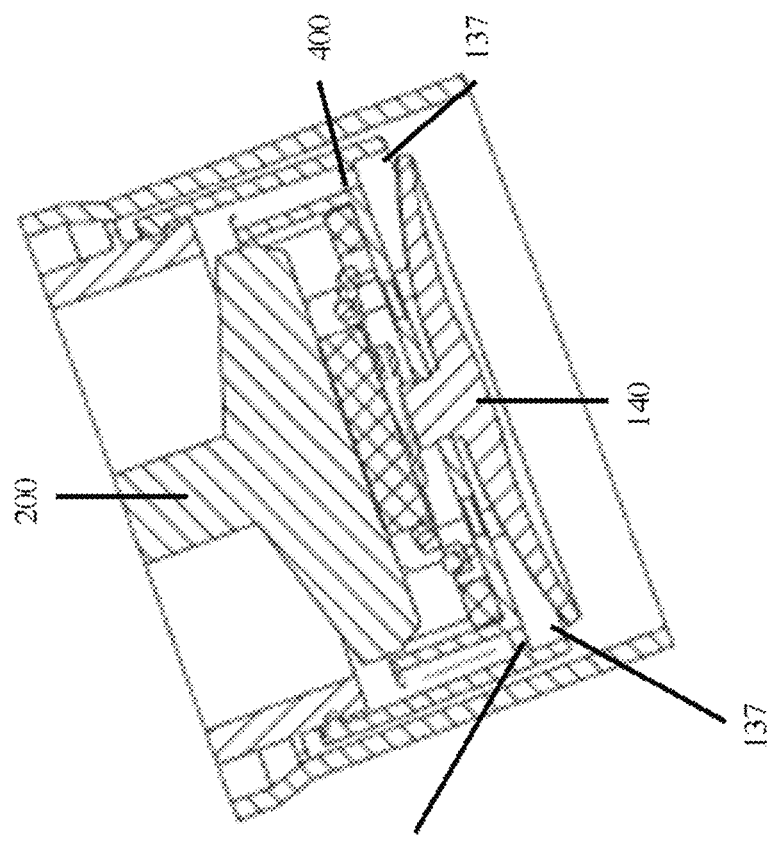
FIG. 19B shows a cross-sectional view of FIG. 18C.
Figure 19A:
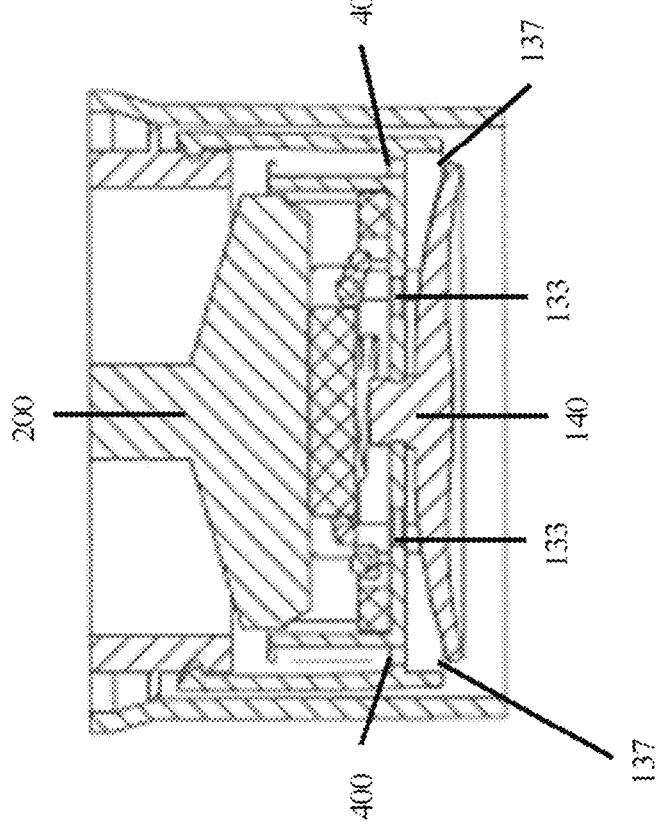
FIG. 19A shows a cross-sectional view of FIG. 18B.
Figure 20A:
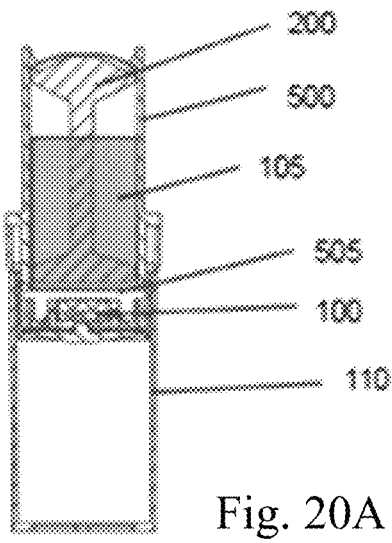
FIG. 20A shows an embodiment of the disclosed assembly in an uncompressed position with formalin in the cap.
Figure 20B:
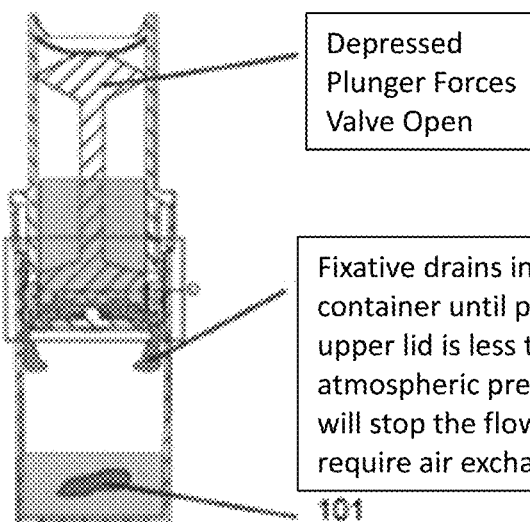
FIG. 20B shows embodiment of the disclosed assembly with gravity-based draining of formalin after puncturing of the seal.
Figure 20C:
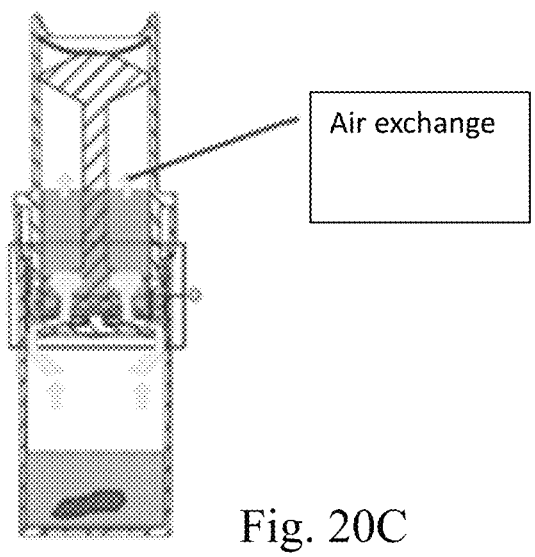
FIG. 20C shows the air flow in the embodiment of the disclosed assembly.
Figure 21A:
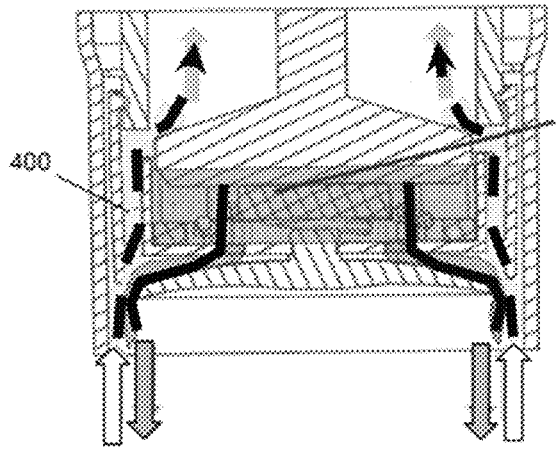
FIG. 21A shows fluid-air exchange of in an embodiment of the disclosed assembly when the fluid volume is low.
Figure 21B:
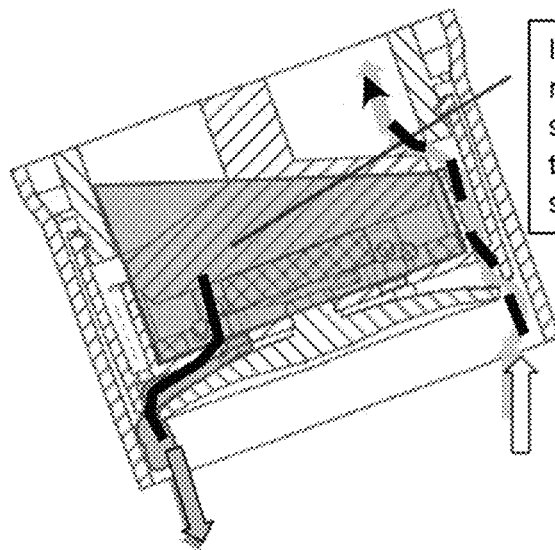
FIG. 21B shows fluid-air exchange at a low fluid volume of the embodiment of the disclosed assembly in a slanted orientation.

FIG. 18 is a schematic of the assembly in closed configuration (FIG. 18A), open configuration while upright (FIG. 18B), and open configuration while tilted (FIG. 18C). FIG. 19 is a close-up of the valve assembly (100) in the open configuration (FIG. 19A), and open configuration while tilted (FIG. 18C). A plurality of air channels (400) are disposed across the periphery of the base (131), while drain apertures (133) are disposed toward the center of the base (131) (see also FIG. 12). At high fluid levels, fluid may flow through the air channels (400) under the force of gravity (FIGS. 20A-20C). When, however, the fluid levels become lower and fluid pressure approaches atmospheric pressure, the air channels (400) provide a fluid-free channel through which air can flow from the sample collection container (110) to the cap (500) in exchange for fluid flowing through the drain apertures (133) (FIG. 21A). In this way, fluid continuously drains into the sample collection container until the container is filled, the cap is completely drained, or the valve is moved back to the closed position. Moreover, a plurality of air channels (400) are provided to permit fluid exchange to continue even when one of the air channels (400) is blocked as a result of tilting (see FIG. 21B).

Figure 22A:
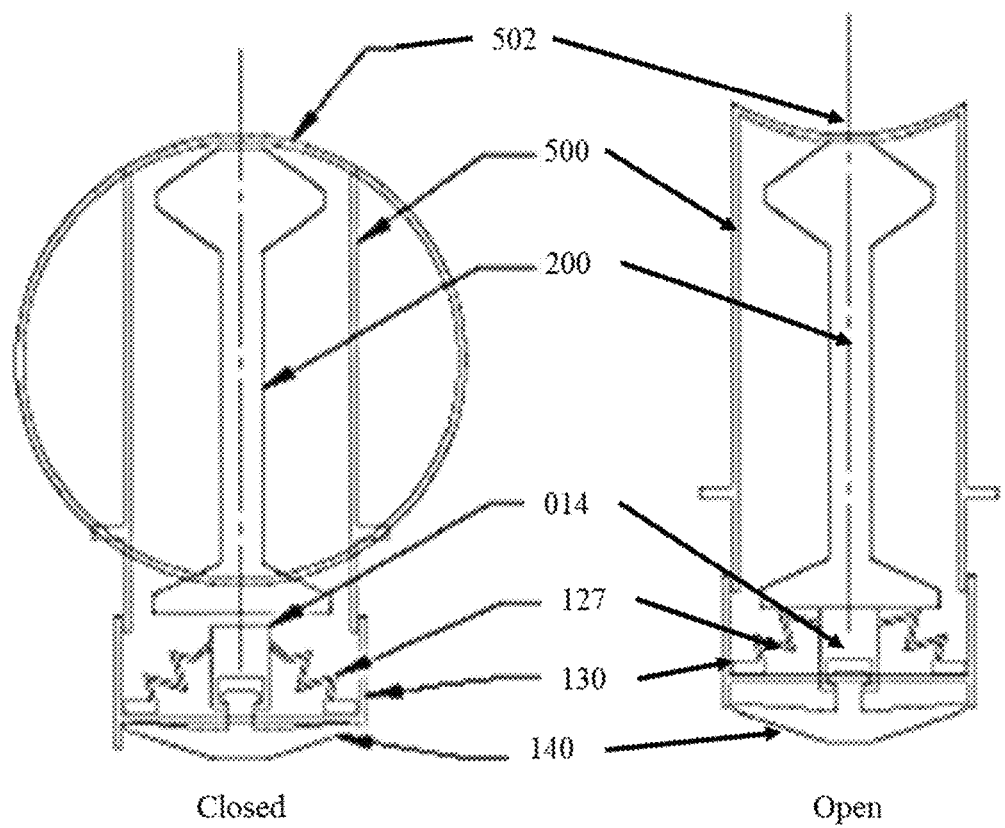
FIGS. 22A-22C show alternate embodiments of the disclosed assembly.
Figure 22B:
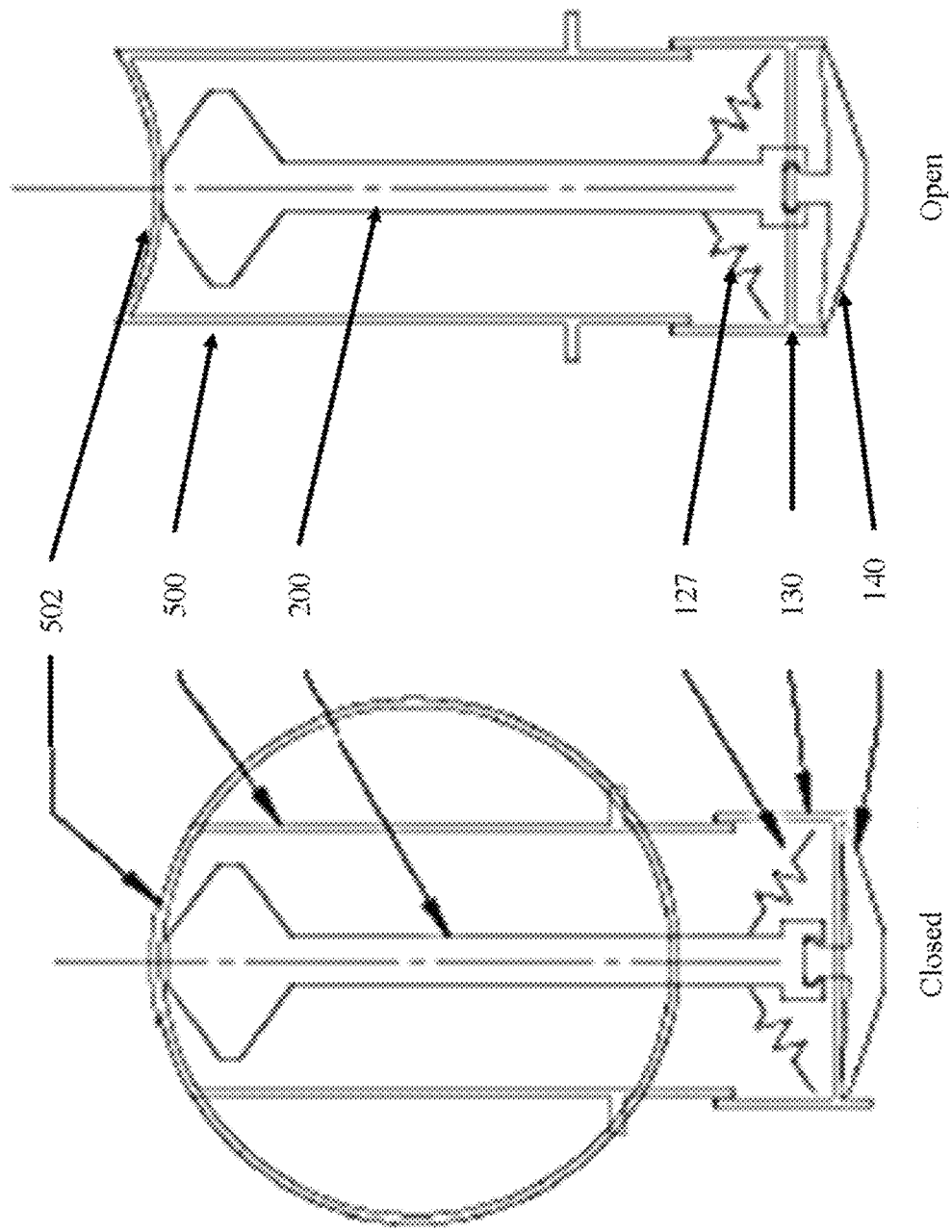
Figure 22C:
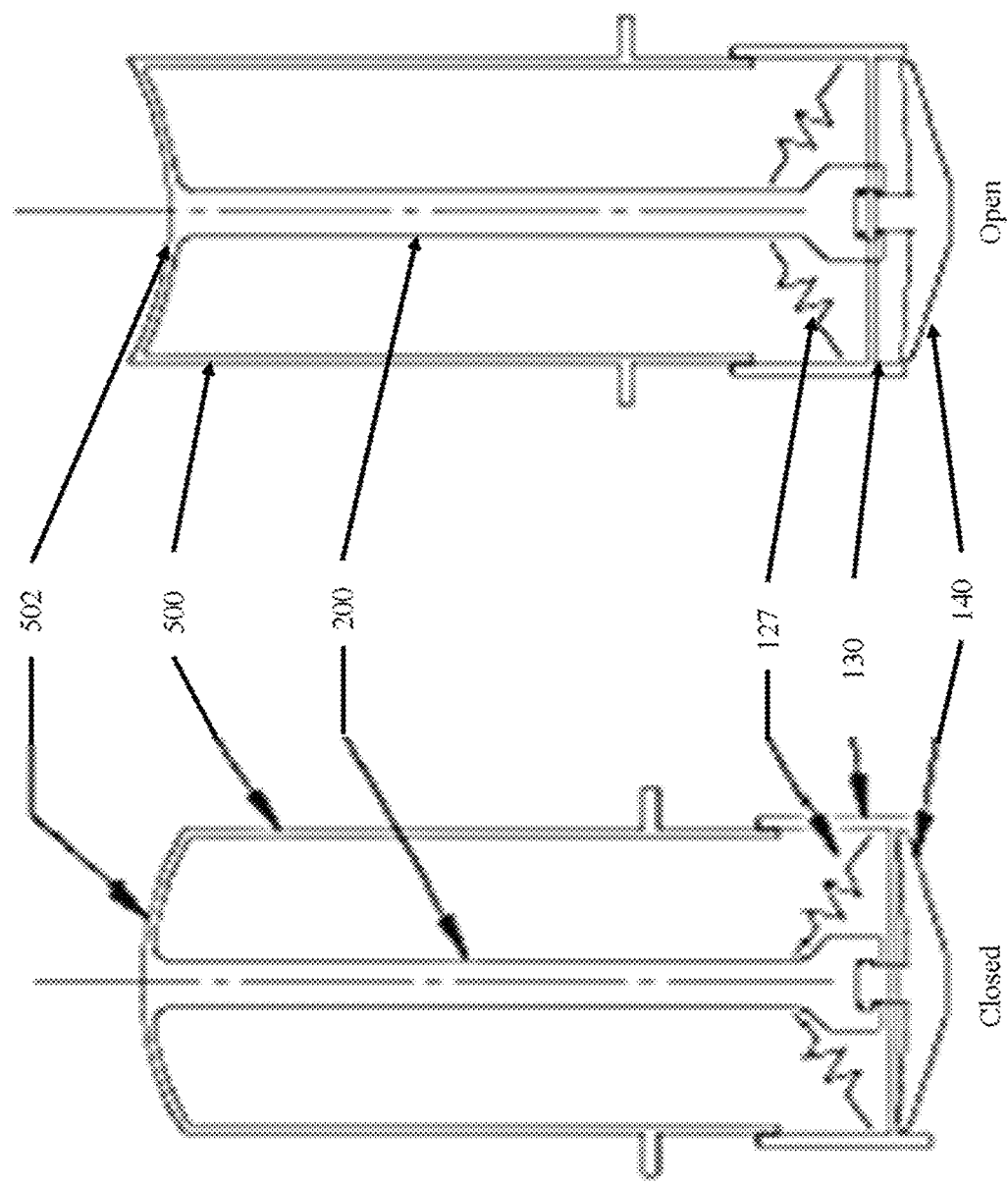

FIG. 22 illustrates an alternative embodiment in which actuation of the actuator causes the valve to translate. In this embodiment, the valve is directly connected to the support structure (122) or the plunger (200), such that pushing the plunger button (502) pushes the entire valve (400) away from the base (131) and into the open configuration. FIG. 22A illustrates an embodiment in which a spring (127) is disposed below the plunger (200), and the valve is connected to the support structure. FIG. 22B illustrates an embodiment in which the spring (127) is attached to the plunger, and the spring (127) is attached directly to the plunger. FIG. 22C illustrates an embodiment of 22B with an alternate plunger shape.

FIG. 23 illustrates an alternate embodiment in which, instead of spring mechanisms (127) attached to an outer frame, a spring mechanism (127) is disposed below the support structure (122).

As used herein, the term "about" refers to plus or minus 10% of the referenced number.

Further embodiments of the present disclosed system and method include the following:

1. A method of preserving a sample (101) in a fluid (105), said method comprising:
   a. providing the sample collection container (110);
   b. providing a valve assembly (100) for preventing backflow of the fluid (105) from the sample collection container (110), said assembly (100) comprising:
      i. a valve actuator flexure (120) comprising:
         an outer frame (121);
         a support structure (122) comprising a support top surface (123), a support bottom surface (124), and at least one arm (125), wherein the arm (125) is disposed on the support bottom surface (124), wherein the arm (125) projects outwardly and away from the support structure (122); and
         at least one spring (127), wherein the spring (127) comprises a first end (128) and a second end (129), wherein the first end (128) of the spring (127) is attached to the outer frame (121), wherein the second end (129) of the spring (127) is attached to the support structure (122);
      ii. a valve housing (130) comprising a base (131), a sidewall (132), at least one drain aperture (133), at least one arm aperture (134), and a stem opening (135), wherein the drain aperture (133), the arm aperture (134), and the stem opening (135) are disposed on the base (131); and
      iii. a valve (140) comprising a valve top surface (141), a valve bottom surface (142), and a valve stem (143) a valve stem (143) disposed on the valve top surface (141), wherein the valve stem (143) has a stopper (144) disposed at a valve stem end, wherein the valve (140) is secured to the valve housing (130) via the stopper (144) inserted through the stem opening (135), wherein the base (131) is positioned between the valve actuator flexure (120) and the valve (140);
   c. placing the sample (101) inside the sample collection container (110);
   d. capping the sample collection container (110) with the valve assembly (100) such that the valve (140) is disposed inside the sample collection container (110);
   e. providing a cap (500), wherein a plunger (200) and a fluid (105) is contained within the cap (500), wherein a primary seal (505) seals the plunger (200) and the fluid (105) inside the cap (500);
   f. attaching the cap (500) to the valve assembly (100) such that the valve actuator flexure (120) is positioned between the base (131) and the cap (500); and
   g. releasing the fluid (105) into the container (110) by depressing the plunger (200) to break the primary seal (505) and push upon the support top surface (123) of the support structure (122) to compress the spring (127), wherein the arm (125) passes through the arm aperture (134) and pushes upon the valve top surface (141), wherein the valve (140) flexes such that the valve top surface (141) is pushed away from the base bottom surface (136), wherein the fluid (105) flows out of the broken seal (505), through the drain apertures (133), and into the sample collection container (110), wherein the fluid (105) contacts the sample (101) in the sample collection container (110).

2. The method of embodiment 1, wherein the valve housing (130) is a cap for the sample collection container (110).
3. The method of embodiment 1, wherein the fluid (105) is a preservative.
4. The method of embodiment 1, wherein the fluid (105) is formalin.
5. The method of embodiment 1, wherein the valve actuator flexure (120) is constructed from a flexible material.
6. The method of embodiment 1, wherein the valve actuator flexure (120) is constructed from an elastomeric material.
7. The method of embodiment 1, wherein the outer frame (121) of the valve actuator flexure (120) is generally ring-shaped.
8. The method of embodiment 1, wherein the outer frame (121) further comprises at least one frame locking tab (301), wherein the valve housing (130) comprises at least one housing locking tab (302) complementary to the frame locking tab (301), wherein the frame locking tab (301) and the housing locking tab (302) prevent the valve actuator flexure (120) from rotating in the valve housing (130).
9. The method of embodiment 1, wherein a plurality of air channels (400) is disposed on the sidewall (132) of the valve housing (130).
10. The method of embodiment 1, wherein the sample (101) is blood, urine, tissue matter, or mucous.
11. The method of embodiment 1, wherein the sample (101) is placed in a cassette, wherein the cassette is placed in the sample collection container (110).
12. The method of embodiment 1, wherein the outer frame (121) of the valve actuator flexure (120) is polygonal in shape.
13. The method of embodiment 1, wherein the valve (140) is selected from the group consisting of an umbrella valve, a duckbill valve, and a check valve.
14. The method of embodiment 1, wherein the valve (140) is generally disc-shaped.
15. The method of embodiment 1, wherein the sample collection container (110) has a gripping component.
16. The method of embodiment 15, wherein the gripping component is an indentation.
17. The method of embodiment 15, wherein the gripping component is a protrusion.
18. The method of embodiment 15, wherein the gripping component is disposed on an external surface of the sample collection container (110).
19. The method of embodiment 15, wherein the gripping component comprises a knurled surface.
20. The method of embodiment 19, wherein the knurled surface comprises an annular ring pattern, a linear knurl pattern, or a diamond knurl pattern.
21. The method of embodiment 1, wherein providing the sample comprises
   a. inserting a sampling device in a body cavity;
   b. collecting the sample from the body cavity with the sampling device, wherein the sample is collected by a sample collecting portion of the sampling device; and
   c. removing the sampling device from the body cavity.
22. The method of embodiment 21, wherein placing the sample (101) inside the sample collection container (110) comprises inserting the sample collecting portion that has the sample into the container (110) and separating the sample collecting portion from the sampling device.

23. A method for processing a sample, said method comprising:
  a. providing a sample collection container (110);
  b. providing a valve assembly (100) for preventing backflow of the fluid (105) from the sample collection container (110), said assembly (100) comprising:
    i. a valve actuator flexure (120) comprising:
      an outer frame (121);
      a support structure (122) comprising a support top surface (123), a support bottom surface (124), and at least one arm (125), wherein the arm (125) is disposed on the support bottom surface (124), wherein the arm (125) projects outwardly and away from the support structure (122); and
      at least one spring (127), wherein the spring (127) comprises a first end (128) and a second end (129), wherein the first end (128) of the spring (127) is attached to the outer frame (121), wherein the second end (129) of the spring (127) is attached to the support structure (122);
    ii. a valve housing (130) comprising a base (131), a sidewall (132), at least one drain aperture (133), at least one arm aperture (134), and a stem opening (135), wherein the drain aperture (133), the arm aperture (134), and the stem opening (135) are disposed on the base (131); and
    iii. a valve (140) comprising a valve top surface (141), a valve bottom surface (142), and a valve stem (143) a valve stem (143) disposed on the valve top surface (141), wherein the valve stem (143) has a stopper (144) disposed at a valve stem end, wherein the valve (140) is secured to the valve housing (130) via the stopper (144) inserted through the stem opening (135), wherein the base (131) is positioned between the valve actuator flexure (120) and the valve (140);
  c. placing a sample (101) inside the sample collection container (110);
  d. capping the sample collection container (110) with the valve assembly (100) such that the valve (140) is disposed inside the sample collection container (110);
  e. providing a cap (500), wherein a plunger (200) and a fluid (105) is contained within the cap (500), wherein a primary seal (505) seals the plunger (200) and the fluid (105) inside the cap (500);
  f. attaching the cap (500) to the valve assembly (100) such that the valve actuator flexure (120) is positioned between the base (131) and the cap (500);
  g. releasing the fluid (105) into the container (110) by depressing the plunger (200) to break the primary seal (505) and push upon the support top surface (123) of the support structure (122) to compress the spring (127), wherein the arm (125) passes through the arm aperture (134) and pushes upon the valve top surface (141), wherein the valve (140) flexes such that the valve top surface (141) is pushed away from the base bottom surface (136), wherein the fluid (105) flows out of the broken seal (105), through the drain apertures (133), and into the sample collection container (110);
  h. contacting the fluid (105) with the sample (101) contained in the sample collection container (110);
  i. placing the sample collection container (110) in a holding well of a carrier assembly;
  j. placing the carrier assembly in a transport assembly; and
  k. transporting the transport assembly from a first location to a second location.

24. The method of embodiment 21, wherein an average temperature of the fluid (105) is at most about 5° C.

25. The method of embodiment 23, wherein the carrier assembly further comprises at least one data logging device.

26. The method of embodiment 25, further comprising detecting and storing time and temperature information associated with the sample (101) in the data logger device of the carrier assembly.

27. The method of embodiment 26, wherein detecting the time and temperature information comprises:
  a. measuring a temperature of the fluid (105) or the sample (101); and
  b. measuring a contact period of time in which the fluid (105) contacts the sample (101); and
  c. storing the temperature and contact period of time measurements.

28. The method of embodiment 26, wherein the time and temperature information associated with the sample (101) is detected while the transport assembly is transported from the first location and the second location.

29. A sample collection system for processing a sample (101) in a fluid (105), said system comprising:
  a. a sample collection container (110), wherein a gripping component is disposed on the sample collection container (110); and
  b. a valve assembly (100) for preventing backflow of the fluid (105) from the sample collection container (110), said valve assembly (100) comprising:
    i. a valve actuator flexure (120) comprising:
      an outer frame (121);
      a support structure (122) comprising a support top surface (123), a support bottom surface (124), and at least one arm (125), wherein the arm (125) is disposed on the support bottom surface (124), wherein the arm (125) projects outwardly and away from the support structure (122); and
      at least one spring (127), wherein the spring (127) comprises a first end (128) and a second end (129), wherein the first end (128) of the spring (127) is attached to the outer frame (121), wherein the second end (129) of the spring (127) is attached to the support structure (122);
    ii. a valve housing (130) comprising a base (131), a sidewall (132), at least one drain aperture (133), at least one arm aperture (134), and a stem opening (135), wherein the drain aperture (133), the arm aperture (134), and the stem opening (135) are disposed on the base (131); and
    iii. a valve (140) comprising a valve top surface (141) and a valve bottom surface (142), wherein the valve (140) is disposed beneath the valve actuator flexure (120) such that the outer frame (121) is positioned between the support structure (122) and the valve (140);
  wherein the valve assembly (100) caps the sample collection container (110), wherein the valve (140) is disposed inside the sample collection container (110).

30. The sample collection system of embodiment 29 further comprising a cap (500) having a plunger (200), a seal (505), and the fluid (105) contained within the cap (500), wherein the primary seal (505) seals the plunger (200) and the fluid (105) inside the cap (500), wherein when the plunger (200) is pressed upon the support top surface (123), the assembly (100) is moved from a first position to a second position, wherein when the assembly (100) is in the second position, the spring (127) is compressed and the arm (125) pushes upon the valve top surface (141), wherein the valve (140) flexes such that the fluid (105) flows through the drain apertures (133) and contacts the sample (101) disposed in the container (10).
31. The sample collection system of embodiment 30, wherein the sample collection system further comprises:
   a. a carrier assembly configured to retain or hold the sample collection container (110); and
   b. a monitoring system comprising a data logging device and at least one sensor configured to obtain, store or transmit one or both of time and temperature information about the sample (101) or fluid (105) in the container (110) when the container (110) is placed in the carrier assembly and transported to a laboratory.
32. The sample collection system of embodiment 30, wherein the gripping component is disposed on an external surface of the sample collection container (110).
33. The sample collection system of embodiment 32, wherein the gripping component comprises an indentation and the carrier assembly comprises a protrusion, wherein the indentation and the protrusion matingly locks the sample collection container (110) in the carrier assembly to prevent displacement of the sample collection container (110).
34. The sample collection system of embodiment 32, wherein the gripping component comprises a protrusion and the carrier assembly comprises an indentation, wherein the protrusion and the indentation matingly locks the sample collection container (110) in the carrier assembly to prevent displacement of the sample collection container (110).
35. The sample collection system of embodiment 32, wherein the gripping component comprises a knurled surface.
36. The sample collection system of embodiment 35, wherein the knurled surface comprises an annular ring pattern, a linear knurl pattern, or a diamond knurl pattern.
37. The sample collection system of embodiment 29, wherein the sample collection container (110) further comprises a temperature sensor, wherein the sensor transmits a temperature of the fluid (105) contained therein to the monitoring system.
38. The sample collection system of embodiment 29, wherein the sample collection container (110) further comprises a radio frequency identification (RFID) tag and the monitoring system further comprises an RFID reader.
39. The sample collection system of embodiment 29 further comprising a transport container comprising an internal holding compartment for transporting the sample collection container, carrier assembly and monitoring system, wherein the transport container is configured to maintain a temperature of the internal holding chamber at a temperature of about 0° C. to about 20° C. for at least 1 hour.
40. The sample collection system of embodiment 29, wherein when the assembly (100) is in a first position, the spring (127) is in a relaxed state.
41. The sample collection system of embodiment 29, wherein the valve (140) further comprises a valve stem (143) having a bulbous stem end (144), wherein the valve stem (143) is disposed on the valve top surface (141).
42. The sample collection system of embodiment 41, wherein the valve (140) is attached to the valve housing (130) via the bulbous stem end (144), wherein the bulbous stem end (144) secures the valve stem (143) to the valve housing (130).
43. The sample collection system of embodiment 41, wherein the valve (140) is attached to the support structure (122) of the valve actuator flexure (120) via the bulbous stem end (144), wherein the bulbous stem end (144) secures the valve stem (143) to the support structure (122).
44. The sample collection system of embodiment 41, wherein the valve (140) is attached to a plunger (200) via the bulbous stem end (144), wherein the bulbous stem end (144) secures the valve stem (143) to the plunger (200).
45. The sample collection system of embodiment 29, wherein the fluid (105) is formalin.
46. The sample collection system of embodiment 29, wherein the sample is collected by a sampling device and placed inside the sample collection container (110).
47. The sample collection system of embodiment 29 further comprising a cassette, wherein the sample (101) is disposed in the cassette, wherein the cassette is disposed in the sample collection container (110).
48. The sample collection system of embodiment 29, wherein the sample (101) is a blood, urine, tissue, or mucous sample.
49. The sample collection system of embodiment 29, wherein the valve actuator flexure (120) is constructed from a flexible material.
50. The sample collection system of embodiment 29, wherein the valve actuator flexure (120) is constructed from an elastomeric material.
51. The sample collection system of embodiment 29, wherein the outer frame (121) of the valve actuator flexure (120) is generally ring-shaped.
52. The sample collection system of embodiment 29, wherein the outer frame (121) of the valve actuator flexure (120) is polygonal in shape.
53. The sample collection system of embodiment 29, wherein the valve (140) is selected from the group consisting of an umbrella valve, a duckbill valve, and a check valve.
54. The sample collection system of embodiment 29, wherein the valve (140) is generally disc-shaped.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described in the description of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions using the phrase "comprising" includes embodiments that could be described as "consisting of", and as such the written description requirement for claiming one or more embodiments using the phrase "consisting of" is met.

The reference numbers recited in the above-described embodiments are solely for ease of examination of this patent application, and are exemplary, and are not intended in any way to limit the scope of the claims to the particular features having the corresponding reference numbers in the drawings.

The invention claimed is:

1. An assembly for storing and transporting biological samples immersed in a fixative solution, the assembly comprising:
    a cap comprising a first chamber prefilled with a volume of a fixative solution;
    a sample container comprising a second chamber for holding the biological sample; and
    a valve assembly comprising (i) a valve disposed between the first and second chambers and in communication with at least one resilient mechanism; and (ii) an actuator;
        Wherein the valve is movable between at least a closed configuration and an open configuration, wherein the resilient mechanism maintains the valve in the closed configuration until a first removable force is applied to the valve, and wherein:
            when the valve is in the open configuration, one or more channel(s) is formed between the first and second chamber permitting fixative solution to flow from the first chamber to the second chamber, and allow air to be vented in exchange;
            when the valve is in the closed configuration, the valve creates a barrier between the first chamber and the second chamber that prevents flow of the fixative solution from the second chamber to the first chamber; and
        wherein the actuator is moveable between at least a disengaged position and an engaged position, wherein when in the engaged position, the actuator is at least partially in contact with at least a portion of the valve disposed between the first and second chambers, and wherein:
            movement of the actuator from the disengaged position to the engaged position requires application of a second force on the actuator by the operator;
            movement of the actuator from the disengaged position to the engaged position applies the first removable force to the valve; and
            removal of the second force from the actuator releases the first removable force from the valve restoring the valve to the closed configuration.

2. The assembly of claim 1, further comprising a machine-readable code.

3. The assembly of claim 2, wherein the machine-readable code is an optical symbology.

4. The assembly of claim 2, wherein the machine-readable code is an electromagnetic pattern and the electromagnetic pattern is provided by a radio frequency identification (RFID) tag on the sample container.

5. The assembly of claim 1, wherein the valve comprises a material having an inherent resiliency, wherein the material having the inherent resiliency forms at least a portion of the barrier between the first chamber and the second chamber when the valve is in the closed position; wherein the first removable force deforms the resilient material in a manner that creates the one or more channels when the valve is in the open configuration; and wherein the inherent resiliency of the material automatically returns the valve to the closed configuration when the first removable force is removed.

6. The assembly of claim 5, wherein the material having the inherent resiliency forms an outer periphery of the barrier, wherein: when the valve is in the closed configuration, the material having the inherent resiliency is in contact with an interior wall of the first chamber, an interior wall of the second chamber, or a valve wall defining an aperture connecting the first chamber and the second chamber, and wherein deformation of the material having the inherent resiliency creates the one or more channels between the material having an inherent resiliency and the interior wall of the first chamber, the interior wall of the second chamber, or the valve wall.

7. The assembly of claim 6, wherein the actuator further comprises one or more rigid members, wherein: movement of the actuator from the disengaged position to the engaged position causes the one or more rigid members to contact a surface of the material having inherent resiliency, thereby exerting the first removable force on the valve.

8. The assembly of claim 7, wherein the one or more rigid members are arranged to exert the first removable force around an outer periphery of the material having inherent resiliency.

9. The assembly of claim 8, wherein the first removable force is exerted equally across the outer periphery of the valve.

10. The assembly of claim 5, wherein the valve is an umbrella valve.

11. The assembly of claim 5, wherein the actuator comprises a plunger, wherein engagement of the actuator causes the plunger to force the volume of the fixative solution toward the valve, thereby causing the fixative solution to exert the first force on the valve.

12. The assembly of claim 11, wherein the valve is a check valve or a duckbill valve.

13. The assembly of claim 1, wherein: the valve comprises: a valve wall defining an aperture connecting the first chamber and the second chamber, and a seal configured such that: when the valve is in the closed configuration, the seal is inside the aperture and in contact with the valve wall to create the barrier between the first chamber and the second chamber; application of the first removable force to the valve causes the seal to move at least partially outside of the aperture to create the channel; and the seal automatically returns to the closed configuration when the first removable force is removed.

14. The assembly of claim 13, the assembly further comprising:
    a second resilient mechanism.

15. The assembly of claim 1, wherein the cap further comprises a frangible seal disposed in the first chamber in a manner to sequester the fixative solution away from the valve, wherein movement of the actuator from the disengaged position to the engaged position breaks the frangible seal and applies the first removable force to the valve.

16. The assembly of claim 1, wherein the resilient mechanism comprises a spring.

17. The assembly of claim 1, wherein the resilient mechanism comprises a valve stem.

18. The assembly of claim 1, wherein the resilient mechanism comprises a magnetic mechanism.

19. An assembly for storing and transporting biological samples immersed in a fixative solution, the assembly comprising:
    a cap comprising a first chamber prefilled with a volume of a fixative solution;
    a sample container comprising a second chamber for holding the biological sample;
    a check valve disposed between the first chamber and the second chamber, wherein the check valve is selected from the group consisting of a ball check valve, a swing check valve, and a tilting disc check valve, wherein:
        when the check valve is in the open configuration, one or more channel(s) is formed between the first and second chamber permitting fixative solution to flow from the first chamber to the second chamber, and allow air to be vented in exchange;

when the check valve is in the closed configuration, the valve creates a barrier between the first chamber and the second chamber that prevents flow of the fixative solution from the second chamber to the first chamber;

the check valve is configured to be in the open configuration when the check valve is upright; and the check valve is configured to be in the closed configuration both when the check valve is in a horizontal position and when the check valve is inerted.

* * * * *